United States Patent
Moazed

(10) Patent No.: US 9,744,237 B2
(45) Date of Patent: Aug. 29, 2017

(54) METHOD AND SYSTEM FOR EFFECTING CHANGES IN PIGMENTED TISSUE

(76) Inventor: Kambiz Thomas Moazed, New York, NY (US)

( * ) Notice: Subject to any disclaimer, the term of this patent is extended or adjusted under 35 U.S.C. 154(b) by 0 days.

(21) Appl. No.: 13/373,797

(22) Filed: Nov. 30, 2011

(65) Prior Publication Data

US 2012/0207809 A1    Aug. 16, 2012

Related U.S. Application Data

(63) Continuation-in-part of application No. 13/138,260, filed as application No. PCT/US2010/000257 on Jan. 29, 2010, now abandoned, application No. 13/373,797, which is a continuation-in-part of application No. 13/261,047, filed as application No. PCT/US2010/002051 on Jul. 21, 2010, now abandoned.

(60) Provisional application No. 61/206,391, filed on Jan. 29, 2009, provisional application No. 61/212,722, filed on Apr. 15, 2009, provisional application No. 61/271,498, filed on Jul. 22, 2009, provisional application No. 61/271,961, filed on Jul. 29, 2009, provisional application No. 61/343,558, filed on Apr. 30, 2010, provisional application No. 61/418,570, filed on Dec. 1, 2010.

(51) Int. Cl.

| | | |
|---|---|---|
| *A61P 27/02* | (2006.01) | |
| *A61K 45/06* | (2006.01) | |
| *A61K 9/00* | (2006.01) | |
| *A61K 31/05* | (2006.01) | |
| *A61K 31/13* | (2006.01) | |
| *A61K 31/352* | (2006.01) | |
| *A61K 31/7088* | (2006.01) | |
| *A61K 33/24* | (2006.01) | |
| *A61K 33/26* | (2006.01) | |
| *A61Q 1/00* | (2006.01) | |

(52) U.S. Cl.
CPC ............ *A61K 45/06* (2013.01); *A61K 9/0048* (2013.01); *A61K 9/0051* (2013.01); *A61K 31/05* (2013.01); *A61K 31/13* (2013.01); *A61K 31/352* (2013.01); *A61K 31/7088* (2013.01); *A61K 33/24* (2013.01); *A61K 33/26* (2013.01); *A61Q 1/00* (2013.01)

(58) Field of Classification Search
USPC ........ 435/6, 91.1, 91.31, 455, 458; 514/1, 2, 514/44; 424/9.1, 9.2, 62, 427, 641; 536/23.1, 24.5; 977/773, 906
See application file for complete search history.

(56) References Cited

U.S. PATENT DOCUMENTS

| | | | | |
|---|---|---|---|---|
| 6,359,001 | B1 * | 3/2002 | Drago | 514/530 |
| 6,495,524 | B1 * | 12/2002 | Hattori et al. | 514/27 |
| 2007/0224346 | A1 * | 9/2007 | Wojtaszek et al. | 427/229 |
| 2009/0087459 | A1 * | 4/2009 | First | 424/239.1 |
| 2011/0003003 | A1 * | 1/2011 | Goldberg et al. | 424/490 |
| 2012/0265149 | A1 * | 10/2012 | Lerner et al. | 604/190 |

OTHER PUBLICATIONS

Laties, et al., Nature, vol. 255, pp. 152-153 (1975).*
Fujita et al., J. Investigative Dermatol., vol. 129, pp. 1489-1499 (2008).*
Kokkinou et al., Pigment Cell Res., vol. 17, pp. 515-518 (2004).*
Hilgenbrink et al., J. Pharm. Sciences, vol. 94, No. 10, pp. 2135-2146 (2005).*
Chancy et al., J. Biol. Chem., vol. 275, No. 27, pp. 20, 676-20, 684 (2000).*
Briganti et al (Pigment Cell Res., vol. 16, pp. 101-110 (2003).*
Kim et al (Cellular and Molecular Life Sci., vol. 62, pp. 1707-1723 (2005).*
Paroo et al, Trends in Biotech., vol. 22, No. 8, pp. 390-394 (2004).*
Jang et al, Expert Rev. Medical Devices, vol. 1, No. 1, pp. 127-138 (2004).*
Opalinska et al, Nature Rev., vol. 1, pp. 503-514 (2002).*

* cited by examiner

*Primary Examiner* — Jane Zara
(74) *Attorney, Agent, or Firm* — David M. McConoughey

(57) ABSTRACT

Methods and systems are described for a rapid and sustainable change in the pigment melanin content of melanocytes of the iris stroma, thereby to change the color of the eye. Also described are compositions for lightening or darkening the pigmented tissues or treating a pigmented tissue disease.

16 Claims, 12 Drawing Sheets

METHOD AND SYSTEM FOR EFFECTING CHANGES IN PIGMENTED TISSUE

CROSS-REFERENCES TO RELATED APPLICATIONS

This application claims the benefit of the priority of
a. International Patent Application No. PCT/US10/00257, filed Jan. 29, 2010, and
b. International Patent Application No. PCT/US10/002051, filed Jul. 21, 2010.
Further, this application claims the benefit of the priority of
c. U.S. NonProvisional Patent Application Ser. No. 13/138,260, filed Jul. 25, 2011 and
d. U.S. NonProvisional patent application Ser. No. 13/261,047, filed Nov. 29, 2011(the 371 of International Patent Application No. PCT/US10/02051).
Further, this application claims the benefit of the priority of
e. U.S. Provisional Patent Application Ser. No. 61/206,391, filed Jan. 29, 2009;
f. U.S. Provisional Patent Application Ser. No. 61/212,722, filed Apr. 15, 2009;
g. U.S. Provisional Patent Application Ser. No. 61/271,498, filed Jul. 22, 2009;
h. U.S. Provisional Patent Application Ser. No. 61/271,961, filed Jul. 29, 2009;
i. U.S. Provisional Patent Application Ser. No. 61/343,558, filed Apr. 30, 2010; and
j. U.S. Provisional Patent Application Ser. No. 61/418,570, filed Dec. 1, 2010.
This application is a continuation in part of
a. International Patent Application No. PCT/US10/00257, filed Jan. 29, 2010;
b. International Patent Application No. PCT/US10/002051, filed Jul. 21, 2010;
c. U.S. NonProvisional Patent Application Ser. No. 13/138,260, filed Jul. 25, 2011;
d. U.S. NonProvisional patent application Ser. No. 13/261,047, filed Nov. 29, 2011(the 371 of International Patent Application No. PCT/US10/02051);
e. U.S. Provisional Patent Application Ser. No. 61/206,391, filed Jan. 29, 2009;
f. U.S. Provisional Patent Application Ser. No. 61/212,722, filed Apr. 15, 2009;
g. U.S. Provisional Patent Application Ser. No. 61/271,498, filed Jul. 22, 2009;
h. U.S. Provisional Patent Application Ser. No. 61/271, 961, filed Jul. 29, 2009;
i. U.S. Provisional Patent application Ser. No. 61/343,558, filed Apr. 30, 2010; and
j. U.S. Provisional Patent Application Ser. No. 61/418,570, filed Dec. 1, 2010.

Throughout this application various publications, published patent applications, and patents are referenced. The disclosures of these documents in their entireties are hereby incorporated by reference into this application in order to more fully describe the state of the art to which this invention pertains.

BACKGROUND OF THE INVENTION

With respect to cosmetic affects, it is known that large populations of people desire to enhance or to change the color of their eyes, skin or hair. As an example, there exists a large market for providing a change or an enhancement of the color of the eyes. Intra-ocular implants have been provided heretofore for the purpose of enhancing or changing the color of the eyes. The markets for hair color-altering compositions and topical applications for bleaching skin discolorations are also huge markets.

Cosmetic treatment of skin and hair color has heretofore been problematic. Multiple topical applications of sometimes-toxic compositions have been required to achieve the desired cosmetic effect, such as a change in color.

In addition, various barriers exist that have heretofore slowed the penetration of active ingredients administered by the ocular route. Both precorneal and corneal factors considerably restrict ocular penetration. The low bioavailability of classical ophthalmic dosage forms can be improved by several approaches, particularly by increasing the time the active ingredients remain in contact with the eye tissues.

Many approaches have been tried, including color contact lenses, implants and laser surgery, to change the color of the eye, none with good results. There is demand for an agent that would safely and effectively change the color of the iris.

With respect to the eyes, a problem exists in that large populations of people are being treated with glaucoma medications derived from prostaglandin analogs. Many such medications cause the conjunctiva to become darker or darkly spotted and the iris of the eye to become darker. These situations often result in unsightly and embarrassing appearance of the eyes. Many people are beginning to experience this problem. This is due at least in part to the aging population in which the prevalence of glaucoma is pronounced. Older people are susceptible to glaucoma and have demonstrated unhappiness with the darkening eye color effect of the glaucoma medications. Usually administered in the form or eye drops. There is a great desire in the general public and as a result a large market for a mechanism to alter the color of the eye from brown to hazel, green, and blue.

There exists a need for a quickly penetrating topical eye medication in by which eye color in healthy people can be changed safely or eye discoloration that resulted from the necessary use of existing glaucoma medications in some people can he reversed. In addition, a medication is needed that overcomes precorneal and corneal factors inhibiting penetration so as to affect the pigmentation of the conjunctiva and iris of the eye by reducing the coloration thereof. There also exists a need for a delivery system for cosmetic or therapeutic chemicals or medications that targets the melanin in pigmented tissue in the eye, the skin, the follicle roots of the hair or the base tissue of the nails so as to be capable of effecting cosmetic changes. For example in the color of the iris, the skin and of the hair, or targeting and delivering treatments for diseases that occur in pigmented tissue without adversely affecting healthy tissue.

SUMMARY OF THE INVENTION

The subject application describes a method of lightening the color of the iris of a human subject. In this method, a composition of a tyrosinase inhibitor is administered to the iris of human subject in an amount effective to lighten the color of the iris. Such composition can also contain at least one melanogenesis inhibitor.

The subject application also describes a method of introducing pigments to the iris of a human subject. In this method, at least one melanogenesis promoter is administered to the iris of a human subject in an amount effective to introduce pigments to the iris. The iris of the human subject becomes darker after such treatment.

The subject application further describes another method of introducing pigments to the iris of a human subject. In this method, a biological dye is administered to the iris of a human subject in an amount effective to introduce pigments to the iris. The iris of the human subject changes color and/or glows after such treatment.

The subject application yet further describes a nanoparticle composition for lightening pigmented tissues. This nanoparticle composition contains a targeting agent of melanocytes chemically bound to a pharmaceutical composition comprising a tyrosinase inhibitor. Such pharmaceutical composition can also contain at least one melanogenesis inhibitor.

The subject application yet further describes a method for lightening pigmented tissues of a human subject. In this method, the nanoparticle composition described herein is administered to the human subject so as to lighten the pigmented tissues.

The subject application yet further describes another nanoparticle composition for treating a pigmented tissue related disease. This nanoparticle composition contains a targeting agent of melanocytes chemically bound to a pharmaceutical composition containing an active agent for the disease.

The subject application yet further describes a method for treating a pigmented tissue related disease. In this method, the nanoparticle composition described herein is administered to a human subject afflicted with a pigmented tissue related disease so as to treat the disease and pigmented cancer cells such as Melanoma. It has been demonstrated that MITF (Microphthalmia-associated transcription factor) is an amplified oncogene of human melanomas and that it also has an oncogenic role in human clear cell sarcoma. MITF is a major contributor of pigment formation in both healthy and cancerous pigmented cells. For these reasons downregulation of the MITF can be applied to both healthy pigmented cells to change the color of the tissue, or to the cancer cells to stop the growth of the tumor.

In the methods described herein, the targeting agent binds to cells of the pigmented tissues to permit the release of the pharmaceutical composition directly into the cells of the pigmented tissue without affecting non-pigmented cells.

The subject application yet further describes a method of depigmenting the iris melanocytes to lighten the color of the iris. This method includes the use of one or more of the following steps:

Blocking the sympathetic and parasympathetic nerve supply to the melanocytes using botulinum toxin and Memantine;
Preventing tyrosine conversion to melanin by one of available tyrosinase inhibitors;
Preventing Melanocyte-stimulating hormone activation (MSH) by using 2,5-Dimethyl-4-hydroxy-3(2H)-furanone (DMHF);
Inhibiting the COX-2 enzyme using NSAIDS;
Preventing melanogenesis by using a cholinergic agonist;
Blocking Alpha I-adrenergic receptors by using antagonist chemicals;
Transcriptional regulation of Melanogenic Enzymes by downregulation of MITE by Transforming Growth Factor (TGF) Family; and
Post-Transcriptional Modification of Melanogenic Enzymes by Inhibiting N-glycolysation of melanosomal enzymes.

DETAILED DESCRIPTION OF THE INVENTION

Figure 1:
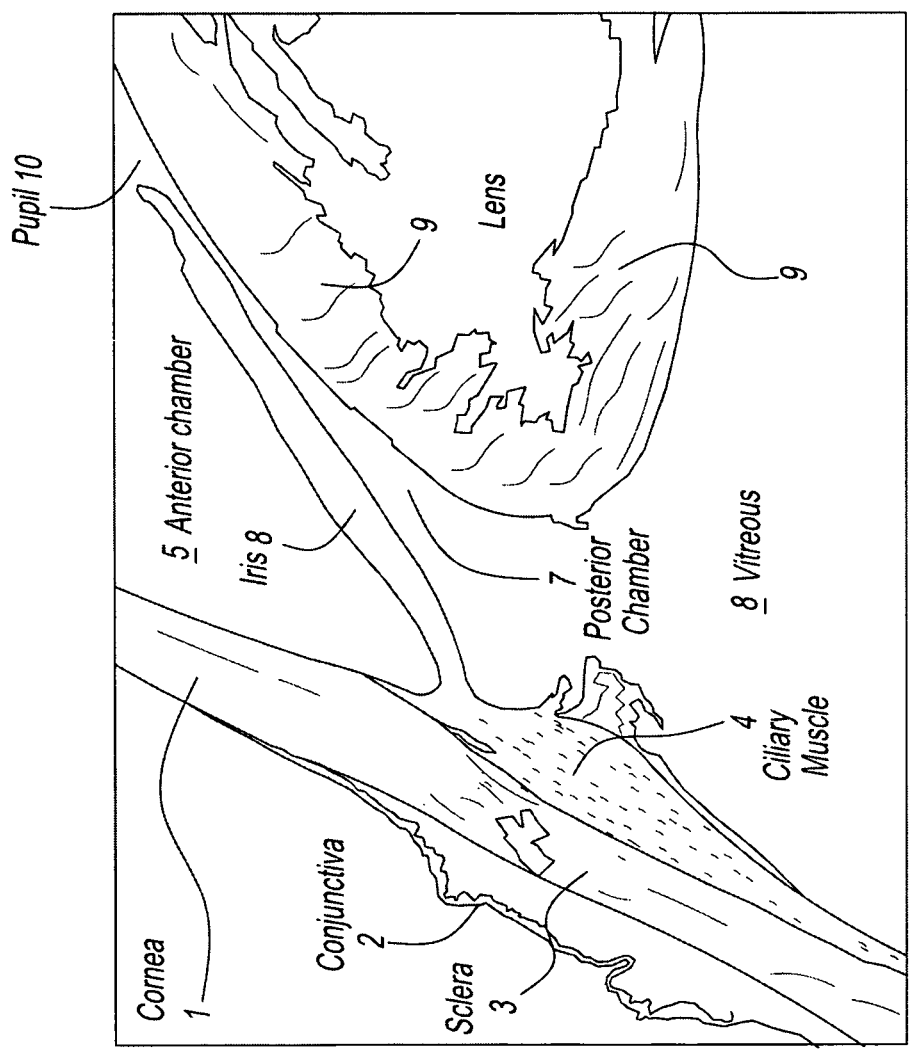
FIG. 1. Background biology of the eye I
FIG. 2. Background biology of the eye II
FIG. 3. Scheme of neuromuscular synaptic junction
FIG. 4. Snap receptors (SNARE) complex and Synapatosomal associated protein (SNAP)
FIG. 5. Target molecules of botulinum (BoNT) and tetanus (TeNT) toxins inside the axon terminal
FIG. 6. Diagram of melanogenesis process
FIG. 7, Melanin formation scheme
FIG. 8. Extracellular influence
FIG. 9. Intracellular pathway from nucleus to melanosomes
FIG. 10. Intracellular pathway from cell membrane to the nucleus
FIG. 11. Schematic of aqueous flow
FIG. 12. The destiny of nanoparticles in the eye
Figure 2:
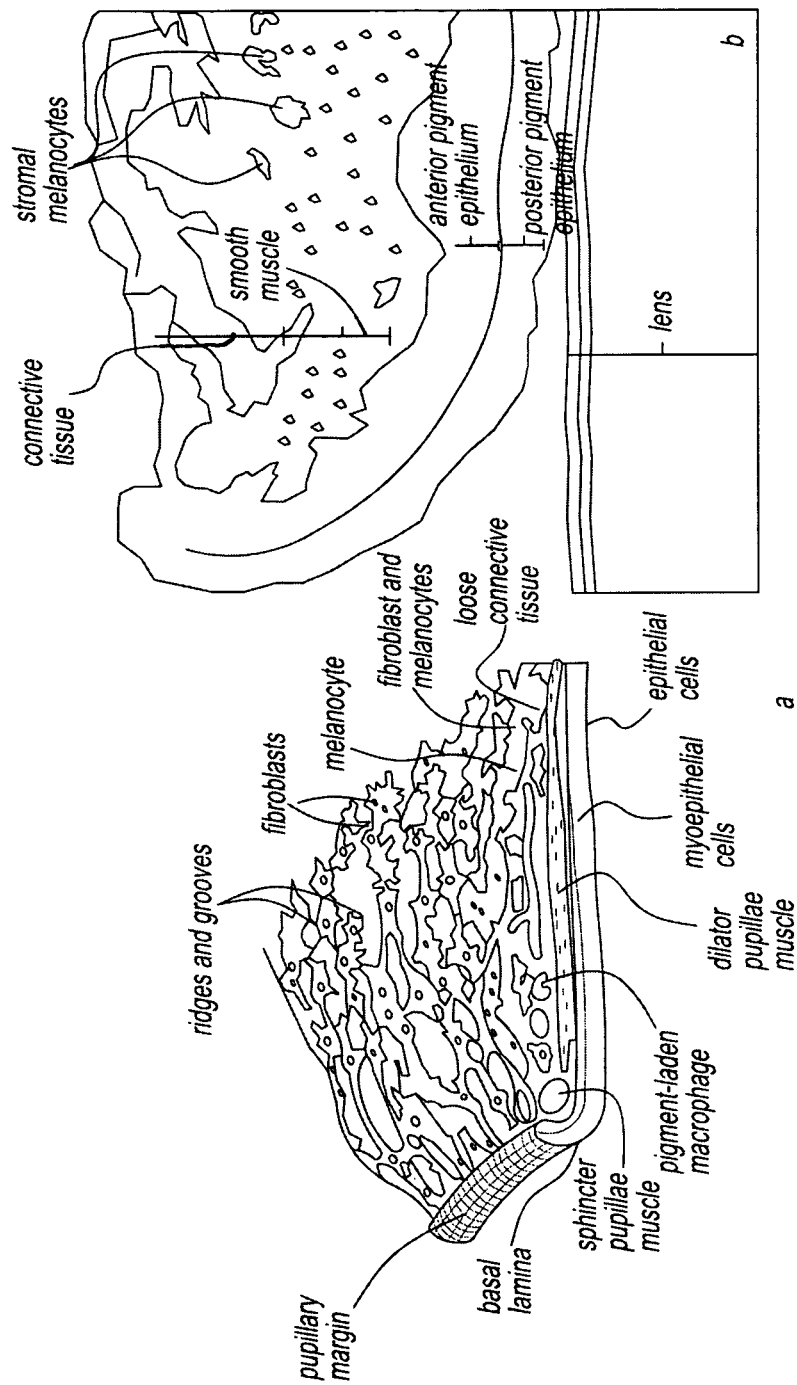
Figure 3:
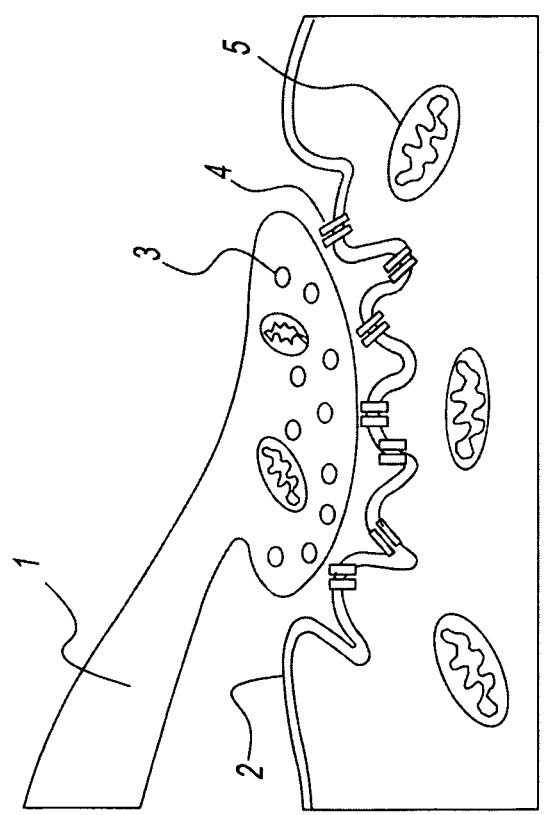
Figure 4:
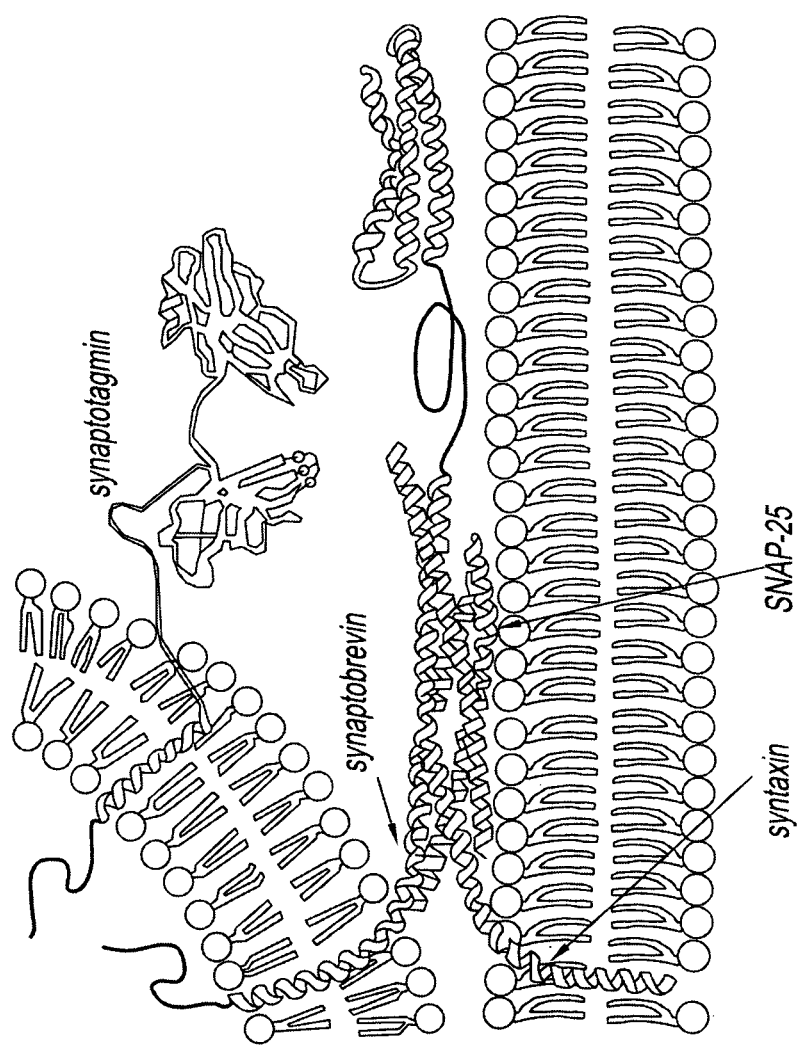
Figure 5:
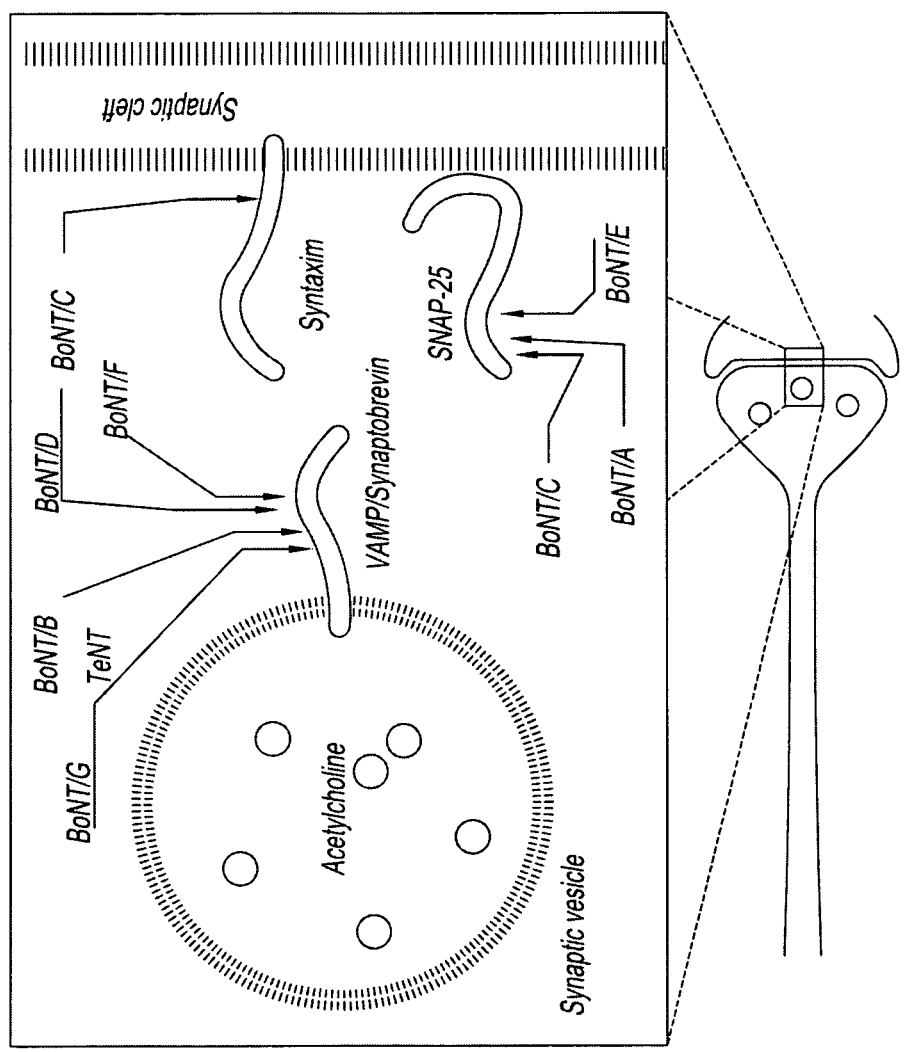
Figure 6:
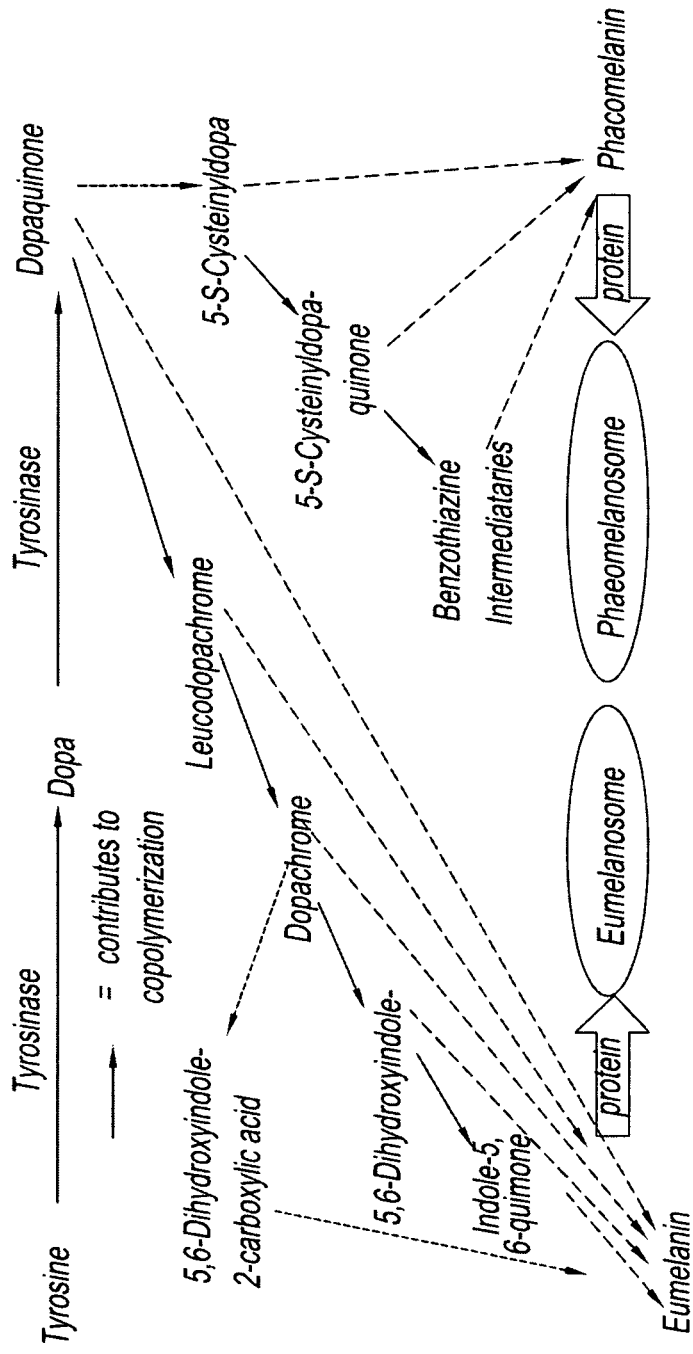
Figure 7:
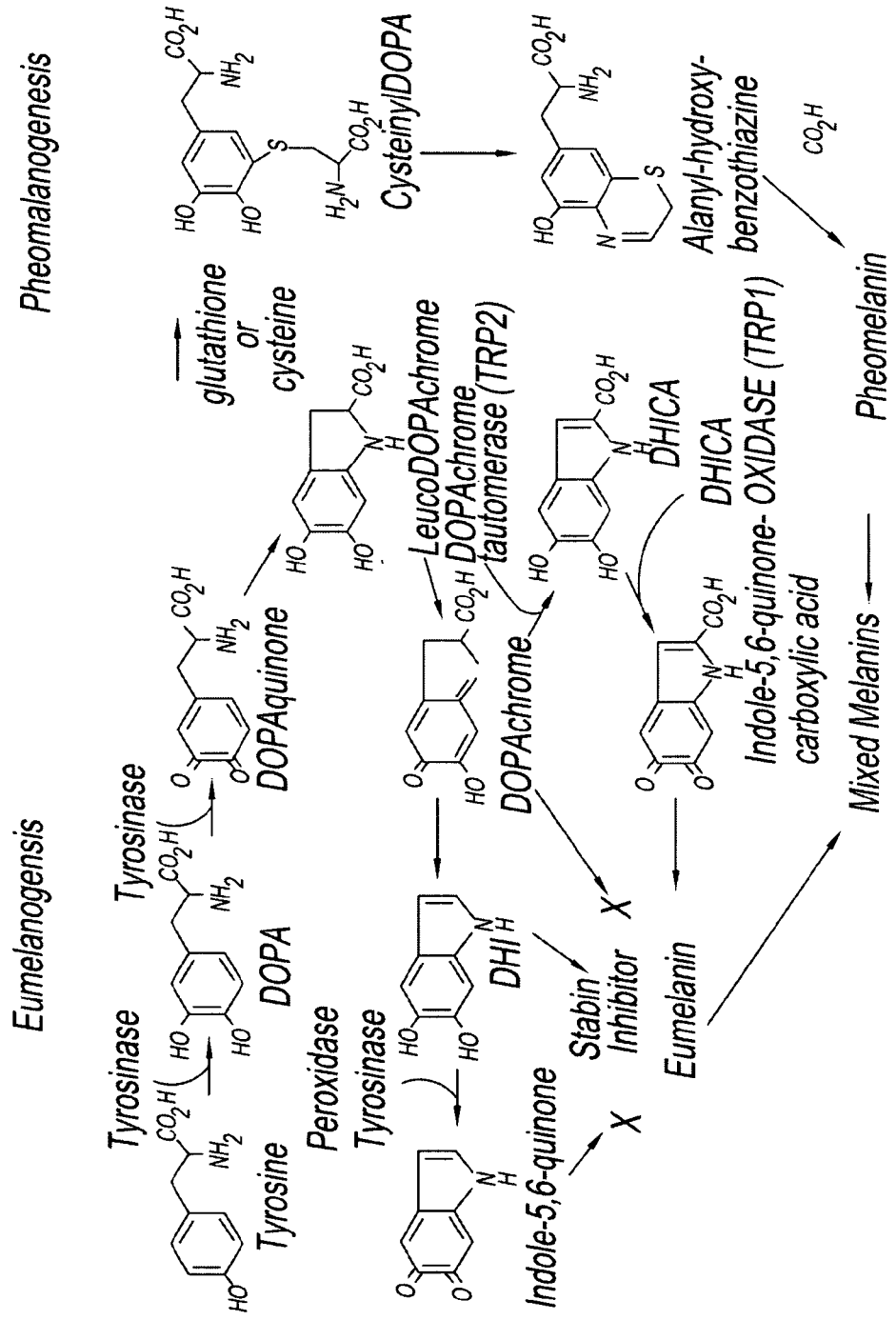
Figure 8:
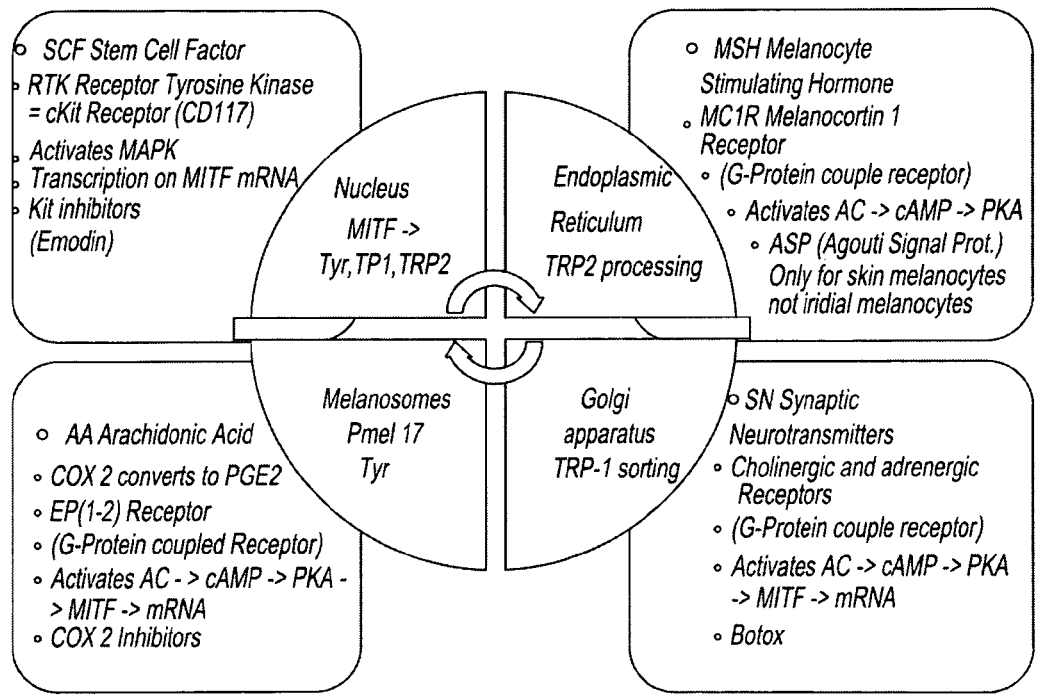
Figure 8:
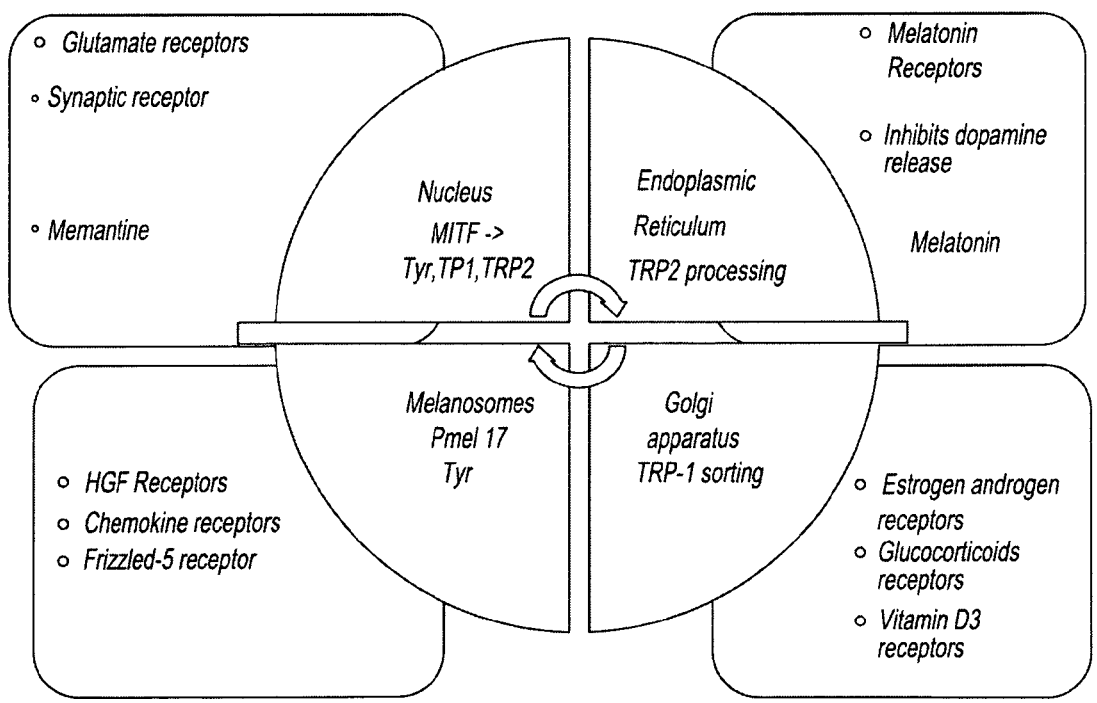
Figure 9:
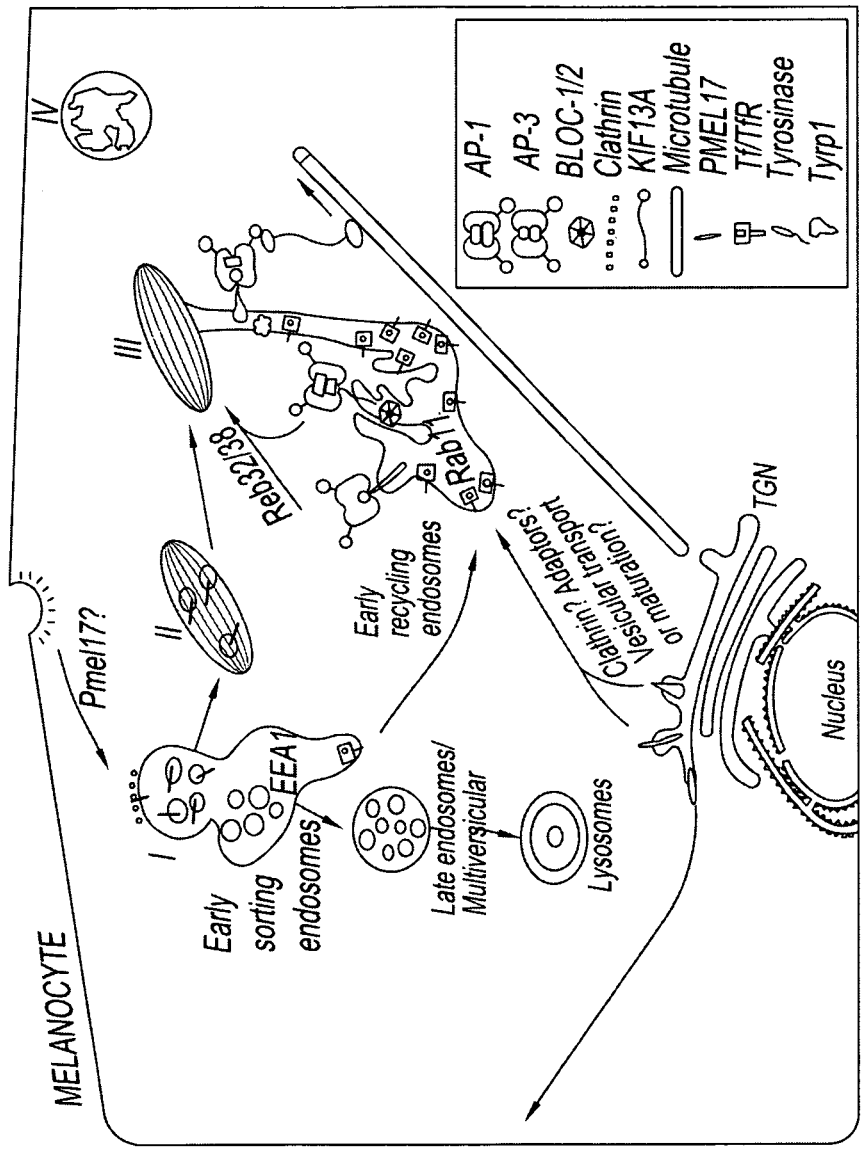
Figure 10:
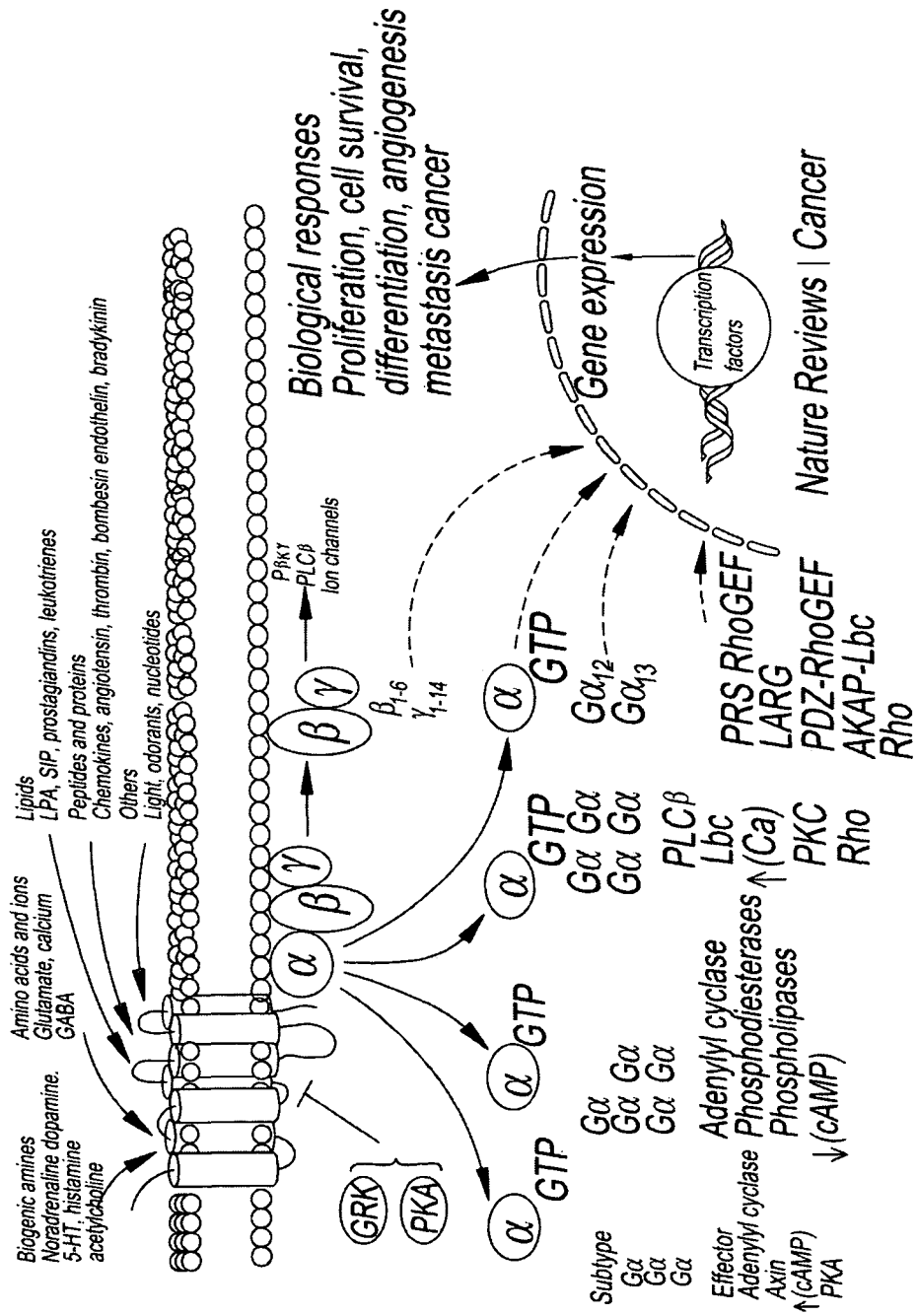
Figure 11:
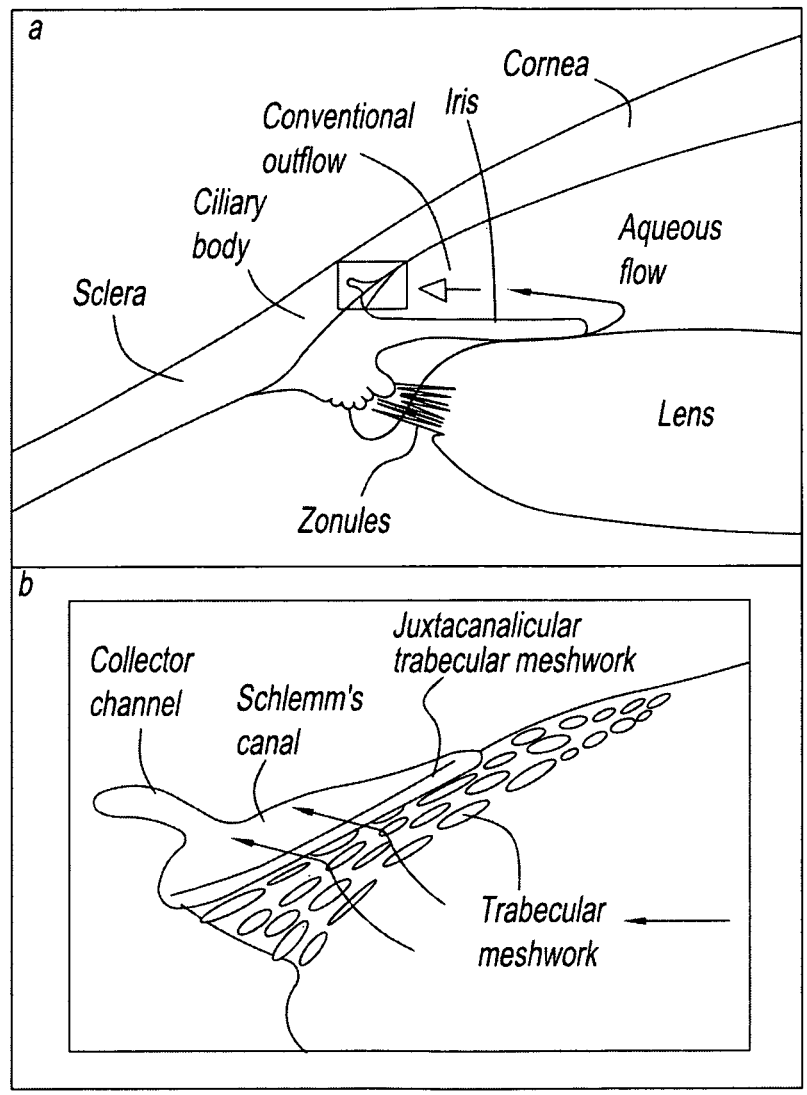
Figure 12:
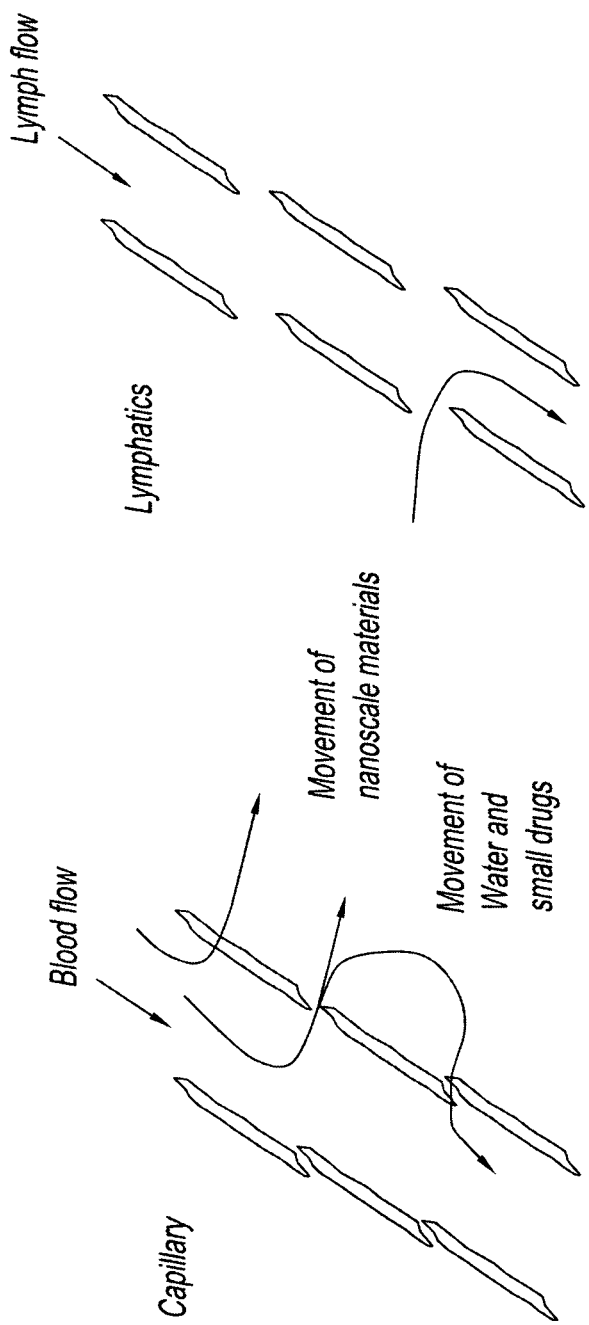

Because eye color is caused by melanin produced by iridial melanocytes, similar strategies to those currently being used to inhibit melanogenesis in the skin may be of benefit, such as tyrosinase inhibition[111] There already exist many skin lightening treatments. however there are major differences between the melanocytes of the iris and melanocytes of the skin, and as such the existing skin treatments do not apply to the eye. Table 1 below provides a list of the major differences between the melanocytes of the iris and melanocytes of the skin. As a result, the depigmenting chemicals (bleaching agents) of the skin may not work directly on the iris.

There is an interesting naturally occurring change in the color of the eye in Homer'Syndrome[3-5], where over a long period of time the color of the iris turns from brown to blue. This is caused by the blockage of the sympathetic nerve impulses to the iris pigment cells (melanocytes) due to many different reasons, such as a tumor or injury. This suggests that stimulation of melanocytes by nerves may also be important for melanogenesis and that inhibition of sympathetic signaling to melanocytes may be effective for causing decreased iridial melanogenesis.

The melanocytes of the iris have direct synaptic attachment with autonomic nerve endings.[1-2] The influence of sympathetic neural stimulation and melanogenesis[3-4] and the color of the iris is a known fact as seen in Horner's syndrome.[3-5] Also, blocking the biosynthesis of melanin through the use of enzymes and bleaching agents may accentuate the process of depigmentation.

TABLE I

The fundamental differences between iris and skin relating to the color

| | | |
|---|---|---|
| 1 | Iris | Skin |
| 2 | No Epithelium on the surface | Epithelium on the surface Ectoderm |
| 3 | Basement Membrane behind the stroma | BM under basal layer |
| 4 | Neural Crest in origin via Mesoderm | N.C. in origin via Surface ectoderm |

TABLE I-continued

The fundamental differences between iris and skin relating to the color

| | | |
|---|---|---|
| 5 | Made of connective tissue and fibrocytes | Made of Basal layer and keratinocytes |
| 6 | Abundant blood vessels and capillaries | No blood vessels or capillaries in the epithelium |
| 7 | Pigment in melanocytes and macrophages | Pigment in melanocytes and keratinocytes |
| 8 | Melanocytes scattered in the stroma | Melanocytes only in Basal layer |
| 9 | Melanin majority "pigment deposits" | Melanin majority melanosomes and keratocytes |
| 10 | Melanin production minimal (stable) | Melanin production constant (very active) |
| 11 | Access barriers (cornea & aqueous) | Access barriers (stratum corneum & spinosum) |
| 12 | Access needs transport system | Access through direct contact |
| 13 | Melanin production minimal or no reaction to UV light exposure | Melanin production very sensitive to UV light exposure |
| 14 | Minimal tyrosinase activity | Tyrosinase very active |
| 15 | Direct innervations to melanocytes | Minimal nerve connection to melanocytes |
| 16 | Melanogenesis is mostly influenced by autonomic neural stimulation | Melanogenesis minimal influence by autonomic nervous system stimulation |
| 17 | Melanocytes do not donate or transfer Melanin to the other cells | Melanocytes constantly donate and transfer melanin to Keratinocytes |
| 18 | Amount of pigment in iris pigment epithelium has nothing to do with the color of the eye | Amount of pigment in skin epithelium is directly related to the color of the skin |
| 19 | Variation in colors not limited to the Melanin alone (Diffraction, light absorption, Interference . . . ). | Color variation directly related to amount of melanin in skin |
| 20 | Pigment in epithelium and stroma | Pigment in basal layer and keratinocytes |
| 21 | COX-2 is endogenous in iris melanocytes | COX-2 is activated by UV exposure or inflammation |
| 22 | No response to alpha-MSH | alpha-MSH causes increased proliferation and melanogenesis |

Due to the fact that melanogenesis is not a linear process, but a cascade of multiple interactive chemical processes, one can intervene at any of multiple steps along the melanogenesis cascade individually, or in combination to reach the desired goal of altering melanin production. By blocking one or more of these steps, and/or by destroying the existing melanin, the bleaching effect can be achieved. For example, the melanocytes of the iris have direct synaptic attachment with autonomic nerve endings[1-2]. The influence of sympathetic neural stimulation and melanogenesis[3-4] and the color of the iris is a known fact as seen in Horner's syndrome[3-5]. Therefore as one of the several factors described below, blocking the neural stimulation to iridial melanocytes in isolation or in combination with blocking the biosynthesis of melanin in iridial melanocytes through the use of enzymes and bleaching agents may accentuate the process of depigmentation.

Melanogenesis is initiated with the first step of tyrosine oxidation to dopaquinone catalyzed by tyrosinase. This first step is the rate-limiting step in melanin synthesis because the remainder of the reaction sequence can proceed spontaneously.[71] The Mequinol (4-hydroxyanisole) subsequent dopaquinone is converted to dopa and dopachrome through auto-oxidation. Dopa is also the substrate of tyrosinase and oxidized to dopaquinone again by the enzyme. Finally, eumelanin are formed through a series of oxidation reactions from dihydroxyindole (DHI) and dihydroxyindole-2-carboxylic acid (DHICA), which are the reaction products from dopachrome.

In one example, a method for achieving the hypopigmentation of the iris, may include one or more of the following steps involving medicinal interventions with small molecules:

1. Block the stimulatory nervous input to the melanocytes using drugs such as, but not limited to, botulinum toxin and memantine.[19-20]

Botulinum toxin can be used to block the synaptic neurotransmitters to prevent melanogenesis by melanocytes, as observed in Horner's Syndrome[3-4-25]. Although many medical uses for botulinum toxin have been documented[19-20] and patented[23-24], the only reference to its cosmetic use in the iris teaches away from such use due to potential side effects on the iridial musculature[28-29]. However, botulinum toxin has been used in the eye for the treatment of strabismus for decades[38], and also retro-bulbar injection was used to treat nystagmus[39] without much adverse effect. Accordingly, the use of drug-containing, targeted nanoparticles described herein could minimize the exposure of neighboring tissues and help prevent complications. This represents a novel use for the botulinum toxin for cosmetic use of pigment alteration in the iridial melanocytes.[26]

Alternatively, NMDA and AMPA glutamate receptor antagonists such as memantine have been shown to be effective in human cells to block nerve stimulation of melanocytes and therefore decrease pigment production and may also be useful for depigmentation.[33]

2. Stop tyrosine conversion to melanin by one of many available tyrosinase inhibitors such as hydroquinone 21, Arbutin[30], hydroxystibene compounds like Resveratrol[31], or zinc alpha-2-glycoprotein.[12]

The activity of tyrosinase in the stroma of the iris is very limited (90% of activity in iris is in pigment epithelium behind iris stroma). Using tyrosinase inhibitors could work alone or in conjunction with other mechanisms of depigmentation to achieve optimal results. Although U.S. Patent Application Publication No. 2000/6359001 (Pharmacia) teaches the use of tyrosinase inhibitors in combination with prostaglandin analogs in order to offset iatrogenic or disease-induced hyperpigmentation in patients being treated for glaucoma, there is no mention of cosmetic use in healthy individuals.

"Hydroquinone, which is a hydroxyphenolic chemical, has been the gold standard for treatment of hyperpigmentation for over 50 years. It acts by inhibiting the enzyme tyrosinase, thereby reducing the conversion of DOPA to melanin. Some of the other possible mechanisms of action are the destruction of melanocytes, degradation of melanosomes, and the inhibition of the synthesis of DNA and RNA."[21]

3. Stop Melanocyte-stimulating hormone (MSH) activation by using DMHF (2,5-Dimethyl-4-hydroxy-3(2H)-furanone).[14]

MSH inhibitors and bleaching agents, when used in combination with the other methods described here, could intensify the bleaching effect and help to achieve the goal of lightening the color of the eye in a shorter span of time.

"Data suggest that DMHF inhibits the downstream step of cAMP production induced by a-MSH, consequently inhibiting melanogenesis. This suggestion was further confirmed by the fact that the increased production levels of microphthalmia-associated transcription factor, tyrosinase and tyrosinase-related protein-1 induced by a-MSH were all reduced by DMHF in B16 melanoma cells. Conclusions: Our study shows that DMHF inhibits a-MSH induced melanogenesis by suppressing CREB phosphorylation, which is induced by protein kinase A, and suggests that DMHF may be an effective inhibitor of hyperpigmentation."[14]

4. Inhibit the COX-2 enzyme using NSAIDs, such as bromfenac, Celecoxib, a COX-2 inhibitor, has been shown to inhibit the increase of melanin.[46]

The majority of COX activity of the iris stroma has been shown to be of the COX-2 version 10. Although COX-2 activity is known to be present in the iris and ciliary body, it has not been realized heretofore that blocking the COX-2 activity by using an NSAID such as bromfenac would create yet another barrier to melanogenesis.

"Little is known about the distribution of COX-1 and COX-2 in animals. In studies investigating the iris and ciliary body of the normal rabbit eye. The presence of COX-1 and COX-2 in freshly excised iris and ciliary body tissue from adult New Zealand White albino rabbits was demonstrated by real-time RT-PCR and Western blot analysis. The localization of both isoforms and of the neuron-specific protein gene product 9.5 was determined by indirect immunofluorescence. Both enzymes are expressed in the iris and the ciliary body."[27]

5. Stop melanogenesis by using a cholinergic agonist. This technique may be especially powerful in combination with neurotoxins from (1), as it could alleviate potential pupillary dilation as a side effect of botulinum administration, for example, but can be reversed by Pilocarpine.

The influence of autonomic neurotransmitters on the uveal melanocytes has been studied and it has been shown that muscarine, a cholinergic agonist, inhibits the growth and melanogenesis in medium, An example of a muscarinic agonist that can be used to interfere with melanogenesis is Pilocarpine, which has been used for many years to treat glaucoma. "Epinephrine, isoproterenol, salbutamol and metaproterenol (adrenergic agonists that can activate $B_2$-adrenoceptors) substantially stimulated growth and melanogenesis of cultured uveal melanocytes in cAMP-deleted medium. Methoxamine, clonidine, prenalterol and D7114 (adrenergic agonists that do not activate B2-adrenoceptors) showed no effect under similar experimental conditions. Muscarine (a cholinergic agonist) inhibited the growth and melanogenesis of uveal melanocytes in complete medium. It indicates that adrenergic agents ($B_2$-adrenoceptor agonists) stimulate growth and melanogenesis in uveal melanocytes, while cholinergic agonist has an inhibitory effect."

6. Additional small molecule agents that decrease tyrosinase activity in iridial melanocytes whose mechanism of action is upstream of tyrosinase synthesis, such as Haginin A, can be useful in achieving depigmentation.

"Haginin A is an effective inhibitor of hyperpigmentation caused by UV irradiation or by pigmented skin disorders through downregulation via ERK and Akt/PKB activation, MITF, and also by the subsequent downregulation of tyrosinase and TRP-1 production.[32]

7. Another approach to decrease melanogenesis is to prevent pH neutralization or promote pH acidification of melanosomes. This could be achieved by blockage of the activity of the P protein, recently shown to be essential for melanosomal pH neutralization.

"near neutral melanosomal pH is optimal for human tyrosinase activity and melanogenesis: (ii) melanin production in Caucasian melanocytes is suppressed by low. melanosomal pH; (iii) the ratio of eumelanin/pheomelanin production and maturation rate of melanosomes can he regulated by melanosomal pH, We conclude that melanosomal pH is an essential factor which regulates multiple stages of melanin production. Furthermore, since we have recently identified that pink locus product (P protein) mediates neutralization of melanosomal pH. We propose that P protein is a key control point for skin pigmentation."[33-34]

8. Amyloid formation in early melanocytes has been shown to be necessary for proper melanogenesis. One example of hypopigmentation subsequent to disruption of normal melanocytic amyloid formation is Pmel 17 blockage, which results in severe hypopigmentation. As such, phorbol ester or a Calmodulin inhibitor may be used to induce Pmel 17 shedding.[65]

"Melanocytes synthesize and store melanin within tissue-specific organelles, the melanosomes. Melanin deposition takes place along fibrils found within these organelles and fibril formation is known to depend on trafficking of the membrane glycoprotein Silver/Pmel 17. However, correctly targeted, full-length Silver/Pmel 17 cannot form fibers. Proteolytic processing in endosomal compartments and the generation of a lumenal alpha fragment that is incorporated into Amyloid-like structures is also essential. Dominant White (DWhite), a mutant form of Silver/Pmel 17 first described in chicken, causes disorganized fibers and severe hypopigmentation due to melanocyte death.[35]

9. Misdirection of tyrosinase to lysosomes to accelerate its degradation. Inulavosin, a melanogenesis inhibitor, misguides tyrosinase from going to melanosomes to going to lysosomes, where the tyrosinase is destroyed. "Inulavosin, a melanogenesis inhibitor isolated from Inula nervosa (Composite), reduced the melanin content without affecting either the enzymatic activities or the transcription of tyrosinase, tyr, or Trp1 in B16 melanoma cells. Inulavosin inhibits melanogenesis as a result of mistargeting of tyrosinase to Ivsosomes.[37]

In addition to the methods outlined above in this application, combinatorial approaches with other effective strategies may be desired in parallel or in series for enhanced timing or strength of effect. For example, molecular biological strategies to silence or decrease specific genetic targets involved in the melanin biosynthetic pathway and/or signaling components that stimulate it could be used with any of the strategies listed above. One example would involve use of inhibitory DNA or RNA agents such as siRNA, as taught in U.S. Patent Application Publication No. 2008/0119433 A1, in combination with agents described in this application, such as botulinum toxin.

10. Targeting of iridial melanocytes. Furthermore, it may be necessary to target the melanocytes specifically, as off-target drug effects may be detrimental. There have been many instances of Nanoparticle Drug Delivery Systems (DDS) that transport toxic medications safely to targeted tissue without affecting the surrounding tissue. Examples includes TB drug delivery system[17] cancer treatment 16, and treatment of fungal infections[22].

In multidirectional approaches to decrease iris pigmentation, in addition to inhibition of tyrosinase catalytic activity, other approaches to decrease iris pigmentation include denervation of melanocytes, inhibition of tyrosinase mRNA transcription, aberration of tyrosinase glycosylation and maturation, acceleration of tyrosinase degradation, interference with melanosome PH, maturation and pigment accumulation, and inhibition of inflammation-induced melanogenic response.

In an embodiment, the emphasis is on using a multiple drug approach together with using Botulinum toxin for changing the color of normally brown eyes to lighter colors. In this embodiment, depigmentation of the iris and as a result a change to the color of the eye is achieved by simultaneous and multiple approaches to stop melanogenesis in the melanocytes in the iris stroma. This includes denervation of the melanocytes by botulinum toxin and stopping the melanogenesis by multiple chemicals that interfere with biosynthesis of the melanin, and muscarine effect that has been shown to inhibit growth and melanogenesis in melanocytes in vitro. It has not been known heretofore to use botulinum toxin for altering the color of the eye.

11. Microphthalmia-associated transcription factor (MITF) modification: MITF is a basic helix-loop-helix leucine zipper transcription factor, which acts as a master regulator of melanocyte development[238]. The MITF-M isoform, with the promoter most proximally located upstream to the common exon sequences, is exclusively expressed in melanocytes and is believed to bind the M box regulatory element and transactivate the promoter of tyrosinase, TYRP-1 and TYRP-2, as well as other genes[237]. MITF's multiple functions vary between instructing melanocytes towards terminal differentiation and/or pigmentation and, alternatively, promoting malignant behavior.

MITF is also an amplified oncogene in a fraction of human melanomas and that it also has an oncogenic role in human clear cell sarcoma.[238]

Upon stimulatory binding of a-melanocyte stimulating hormone (a-MSH) to the melanocortin 1 receptor (MC1R), adenyl cyclase is activated and cAMP produced. cAMP then activates the protein kinase A (PKA) pathway to phosphorylate cAMP-responsive element binding protein (CREB) transcription factors, which mediates MITF-M promoter activation to induce melanogenesis. MITF is also regulated at the transcriptional level by interleukin-6 (IL-6) and Wnt Signaling pathway. Furthermore. MITF is post-transcriptionally regulated by phosphorylation via ribosomal S6 kinase (RSK), glycogen synthase kinase-3b (GSK3b), p38 stress signaling and mitogen-activated protein kinase (MAPK) pathways by currently undefined mechanisms/pathways.

Glycogen synthase kinase 3B (GSK3B) is implicated in many biological events, including embryonic development, cell differentiation, apoptosis, and the insulin response. GSK3B also plays a key role in the Wnt/B-catenin pathway. The master regulator of the pigmentation microphthalmia-associated transcription factor (MITF) is a target for the Wnt pathway 243.

a. Using Transforming growth factor-B (TGF-beta) to down regulate MITF: Transforming growth factor-(TGF-beta1) is a cytokine that plays a role in the inhibition of pigmentation.

TGF-beta1 is believed to mediate the down-regulation of the MITF promoter activity, reducing the production of tyrosinase, TYRP-1, TYRP-2 and MITF protein levels[239].

TGF-beta1 inhibits the expression of paired-box homeotic gene (PAX 3), a transcription factor and key regulator of MITF in melanocytes[240].

TGF-beta1 influences the extracellular-signal related kinase (ERK) pathway and down-regulates MITF as well as melanogenic enzyme production[241]

ERK activation by sphingosine-1-phosphate, C2-ceramide and sphingosylphosphorylcholine has also been reported by Kim et al., which the authors hypothesize, may play an important role in the inhibition of melanogenesis ERK activation, is thought to result in phosphorylation of MITF and its subsequent ubiquitination and degradation[242].

b. Using Transforming growth factor-beta (TGF-beta) to down regulate MITF:

Transforming growth factor-beta2 (TGF-beta2) is also a protein encoded by paired-box homeotic gene 3 (PAX3) is a key regulator of the microphthalmia-associated transcription factor (MITF) in the melanocyte lineage.

"PAX3 expression is directly inhibited by TGF-beta/Smads. UV irradiation represses TGF-beta in keratinocytes, and the repression of TGF-beta/Smads upregulates PAX3 in melanocytes, which is associated with a UV-induced melanogenic response and consequent pigmentation. Furthermore, the TGF-beta-PAX3 signaling pathway interacts with the p53-POMC/MSH-MC1R signaling pathway, and both are crucial in melanogenesis. The activation of p53-POMC/MSH-MC1R signaling pathway is required for the UV-induced melanogenic response because PAX3 functions in synergy with SOX10 in a cAMP-response element (CRE)-dependent manner to regulate the transcription of MITF'[240].

The known amount of active TGFbeta2 in aqueous humor (0.2-0.4 ng m1-1) is sufficient to inhibit the growth of uveal melanocytes. It indicates that TGF-beta2 is a potent growth inhibit factor of uveal melanocytes and may play an important role in maintaining the non-proliferative, relatively quiescence status of uveal melanocytes in vivo.[244]

Recently downregulation of MITF has been reported using *Thymelaea hirsuta* extract.[245]

12. Post-Transcription Modification of Melanogenic Enzymes

"Treatment with various agents that inhibit N-glycosylation can result in the down-regulation of melanosomal enzyme activity and reduced melanosomal maturation A major post-translational modification of melanogenic enzymes is the attachment of re-linked glycans to asparagine residues in Asn-X-Ser/Thr motifs (where X is not Pro), during the polypeptides translocation in the ER. This glycosylation is critical for the proper maturation of tyrosinase. A detailed review of the processes involved in the N-glycosylation of melanogenic enzymes has been published by Branza-Nichita el al. Inhibition of proper Nglycan processing of melanogenic enzymes can result in improper polypeptide folding and in turn inhibition of melanogenesis, as they facilitate association with lectin-chaperones.

An alpha-glucosidase inhibitor that disrupts early ER N-glycan processing, and deoxymannojirimycin, an inhibitor of alpha-1,2-mannosidase which are thought to be responsible for late glycan processing, showed inhibition of glycosylation, transportation of tyrosinase to the melanosome and melanin synthesis Using tunicamycin and glucosamine, specific inhibitors of lipid carrier-dependent glycosylation of protein, resulted in decreased pigmentation and ultra structural as well as biochemical aberrations in melanogenic compartments of treated B16 melanoma cells BMY-28565, inhibits melanogenesis by depressing tyrosinase activity with no impact on tyrosinase mRNA levels in B16 melanoma cells.

Other factors explored for their ability to modulate tyrosinase glycosylation include calcium D-pantetheine-S-sulfonate, ferritin and glutathione. Glutathione induced inhibition of tyrosinase glycosylation, blocks the maturation and transfer of tyrosinase from GERL (Golgi-endoplasmic reticulum-lysosome)-coated vesicles to the pre-melanosome. Yet, other mechanisms of action proposed for glutathione include (A) the direct inactivation of tyrosinase by chelating copper within the enzyme's active site. (B) Mediating the transition from eumelanogenesis to pheomelanogenesis, as glutathione participates in the conversion of dopaquinone to pheomelanin, (C) antioxidant properties that quench free radicals and peroxides that induce melanin formation, and (D) modulating the depigmenting capabilities of melanocytotoxic agents.

In a distinct study by Choi et al, treatment of HM3K0 melanoma cells with deoxymannojirimycin, a alpha-glucosidase inhibitor that disrupts early ER N-glycan processing, and deoxymannojirimycin, an inhibitor of alph-1,2-mannosidase which are thought to be responsible for late glycan processing, showed inhibition of glycosylation, transportation of tyrosinase to the melanosome and melanin synthesis"[246].

Such a technique would result in a rapid and sustainable reduction in melanin content of the iris stroma and thereby a lightening of the color of the eye. In an example, a method for achieving the bleaching and/or coloring of the iris, may include administering one or more of the following agents to the eyes of a human subject:

Tyrosinase inhibitor
Glutamate receptor blocker (Memantine)(CAS)
Alpha-adrenergic blocker (Thymoxamine)(CAS)
Cox inhibitor (Bromfenac)
Cholinergic agonist (Pilocarpine)(CAO)
Downregulation of mitf, tyr & Trp1 (Haginin A)(CAD)
Acidification of melanosomes.(H89)
Opioid receptor antagonist (Naloxone)
Pmel 17 blocker (Calmodulin inhibitors)
Fibroblast growth factor inhibitor
MITF downregulation (by TGF beta family such as TGF-beta-1 & TGF beta-2)
Post-Translational Modification of Melanogenic Enzymes (N-Glycosylation Inhibitors) siRNA gene silencing The following is a list of tyrosinase inhibitors which can be used for the method for achieving the bleaching and/or coloring of the iris described above.

1. Kojic acid, the most intensively studied inhibitor of tyrosinase, is a fungal metabolite currently used as a cosmetic skin-whitening agent and as a food additive for preventing enzymatic browning[91]. Other slow-binding inhibitors of tyrosinase are the very potent inhibitor tropolone[93] and the substrate analog L-mimosine.[94].

2. New Inhibitors of tyrosinase are classified into five major classes, including polyphenols, benzaldehyde and benzoate derivatives, long-chain lipids and steroids, other natural or synthetic inhibitors, and irreversible inactivators based on either the chemical structures or the inhibitory mechanism.

3. Polyphenols represent a diverse group of compounds containing multiple phenolic functionalities and are widely distributed in nature. Polyphenols are also the largest groups in tyrosinase inhibitors until now.

Flavonoids are among the most numerous and best-studied polyphenols, that is, benzo-||-pyrone derivatives consisting of phenolic and pyrene rings. Widely distributed in the leaves, seeds, bark, and flowers of plants, more than 4,000 flavonoids have been identified to date. Flavonoids may be subdivided into seven major groups, including: flavones, flavonols, flavanones, flavanols, isoflavonoids, chalcones, and catechin. In addition to flavonoids, other polyphenols, which were also identified as tyrosinase inhibitors, contain stilbenes and coumarin derivatives.

Flavonols: quercetin (5,7,3',4'-tetrahydroxyflavonol)[100], myricetin (5,7,3$^1$,4',5'-pentahydroxy-flavonol), kaempferol (5,7,4'-trihydroxyflavono1)[100]. galangin (5,7-dihydroxyflavonol), morin, buddlenoid A, buddlenoid B[98-99] 6-hydroxy-kaempferol.[101]

Flavanones: Norartocarpetin: R=OH (Competitive; RAb, 10.4F)[105], Artocarpetin: R=OCH3(RAb<0.1F)[99], Streppogenin(Competitive; RAb), 13.6F)[107] Flavanols: Dihydromorin (RAb, 0.5F)[99] Taxifolin (RAb,1.0F; ref.46) 000H0H00HR2R3R100H000HOMe0H Isoflavans: Glabridine(Non-competitive; RAb, 15.2F)[117], GlyasperinC (RAb, 27.7F),[117]00H0H0H0H Isoflavones: Calycosin(RAb, 1.3F)[123], 6-Hydroxydaidzein: R1=R3=H, R2=0H(Competitive; RAb, 6.0F)[119], 8-Hydroxydaidzein: R1=R2=H, R3=0H(Suicide substrate)[120], 8-Hydroxygenistein: R1=R3=0H, R2=H(Suicide substrate)[120], Isoflav-3- enOOHOHOOHR, HagininA (Non-competitive; RAb, 10.1F)[121]

Chalcones: 2,4,2',4'-Tetrahydroxychalcone: R=H(Competitive; RAb, 2.5F)[132], 2,4,6,2',4'-Pentahydroxychalcone: R=OH(Competitive; RAb, 12.0F)[132], ROHOOHOHOH Prenylated Chalcones: OHOOHMe0LicochalconeA (Competitive; RAb, 5.4F)[124], OHOOHOHOHTMBC (Competitive; RAb, 26.1F)[127],-17OHOOHOHOMeOHO-HOOHOHOMeOHOHKuraridin(RAb, 34.1 F)[125], Kuraridinol (Non-competetive; RAb,18.4f)[126]

N-Benzylbenzamides: NHOR1R2R3R4R5OH3,5,2',4'-Tetrahydfoxyl derivatives: R1=R3=H,R2=R4=R5=OH (RAa, 7.4F)[133], 2,4,2',4¹-Tetrahydroxyl derivatives: R1=R3=R5=OH,R2=R4=H (RAa,0.6F)[133], 3,5,4'-Trihydroxyl derivatives: R1=R3=R5=H, R2=R4=H (RAa<<0.1F)[133], 2,4,4'-Trihydroxyl derivatives: R1=R3=0H, R2=R4=R5=H (RAa<<0.1F)[133]

Flavones, flavanones, and flavanols, nobiletin (5,6,7,8,3',4'-hexamethoxyflavone), naringin (5,7.4'-trihydroxyflavanone), neohesperidin (5,7,3'-trihydroxy-4'-methoxyflavone)[102-103], neohesperdin in citrus fruit, Mulberroside F (moracin M-6,3'-di-O-[ ]-glucopyranoside), norartocarpetin, Streppogenin (5,7,2',4'-tetrahydroxy-flavavone,)[107], Dihydromorin (5,7,2',4')-tetrahydroxyflavanol, Artocarpetin (5,2',4'-trihydroxy-7-methoxyflavone, isolated from the wood of *Artocarpus heterophyllus*[106-107], taxifolin (5,7,3'4)-tetrahydroxyflavanol[113], *Garcinia subelliptica*[114].

Isoflavonoids: seeds of *Glycyrrhiza* species (Leguminoseae): glabridin and glabrene[115], Glyasperin C[117], *Aspergillus oryzae* containes three hydroxyisoflavones-6-hydroxydaidzein (6,7,4'-trihydroxyisoflavone); -8-hydroxydaidzein (7,8,4'-trihydroxyisoflavone); and -8-hydroxygenistein (5,7, 8,4'- tetrahydroxyisoflavone)[118-119], Haginin A (2',3'-dimethoxy-7,4'-dihdroxyisoflav-3-ene[121], Dalbergioidin (5,7,2', 4'-tetrahyroxyisoflavan) isolated from *L. cyrtobotrya*[122], calycosin (4'-methoxy-7,4'-dihydroxyisoflavone[123].

Chalcones: Three chalcones derivatives, including licuraside, isoliquiritin, and licochalcone A, kuraridin, isolated from the plant *Sophora flavescens* kuraridinol, 2,4,2',4'-tetrahydroxy-3-(3-methy1-2-buteny1)-chalcone (TMBC), 2,4,2',4'- tetrahydroxychalcone.[131]

Stilbenes: Oxyresveratrol (2,4,3',5'-tetrahydroxy-trans-stilbene)[106], Resveratrol (2,3',5'-trihydroxy-trans-stilbene), Chloroporin (4-gerany1-3,5,2',4'-tetrahydroxytrans-stilbene)[136], Gnetol (2,6,3',5'-tetrahydroxy-trans-stilbene)[137], piceatannol (3,5,3',4'-tetrahydroxy-trans-stilbene)[138], Dihydrognetol[139], HNB [4-(6-hydroxy-2-naphtyl)-1.3-bezendiol] New isostere of oxyresveratrol, HNB is the strongest tyrosinase inhibitor published until now.[145]

Coumarins: Aloesin[146-147], Esculetin[147], 9-hydroxy-4-methoxypsoralen 8'-epi-cleomiscosin A[151], cleomiscosin A, Benzaldehyde and Benzoate Derivatives: benzoic acid, benzaldehyde, anisic acid, anisaldehyde, cinnamic acid, and methoxycinnamic acid from the roots of *Pulsatilla ceruna*[151], 4-substituted benzaldehydes from cumin[153], 2-hydroxy-4-methoxybenzaldehyde from roots of *Mondia whitei*[154], p-coumaric acid from the leaves of *Panax ginseng*[155], hydroxycinnamoyl derivatives from green coffee beans[156], and vanillic acid and its derivatives from black rice bran[157], Ilourobentaldehydes[161], methyl trans-cinnamate[162], salicylic acid[163], Hydroxybenzaldehydes[164], 4-[ ]-D-glucopyranosyloxybenzoate[165], Protocatechualdehyde[166-167], Vinylbenzaldehyde[168]. 4-alkylbenzaldehyde[169-170], 2-hydroxy-4-isopropyl-benzaldehyde[171], 3,4-dihydroxybenzaldehyde-O-ethyloxime[172], 4-butyl-benzaldehyde thioseinicarbazone[173], Gallic acid (3,4,5-trihydroxybenzoate)[174-176], Gallic acid was also found to be very toxic to melanoma cells with cytotoxicity comparable to that of hydroquinone[177], flavonoids with gallate moiety bonded to the 3-hydroxyl position, including GCG [(+)-gallocatechin-3-0-gullate] and EGCG [(−)-epigallocatechin-3-0-gallate], were isolated from green tea leaves[179], Syntetic tyrosyl gallates[180], 1,2,3,4,6-pentagalloylglucopyranose isolated from the seed kernels of *M. indica*[17], 1,2,3,4,6-pentagalloylglucopyranose isolated from the seed kernels of *M. indica*[178], *Paeonia suffruticosa*.[181]

Long-chain Lipids and Steroids: Several lipids were purified from natural sources and exhibited tyrosinase inhibitory activity, including Triacylglycerol, trilinolein[182], Glycosphingolipid, soyacerebroside[183], Cerebroside B, from *Phellinus linteus*[166], Trans geranic acid[184], *Trifolium balansae*[185], 2[ ](2S)-hydroxy1-7(E)-tritriacontenoate[186], Triterpenoid, 3.21,22,23-tetrahydroxycycloart-24(31),25(26)-diene[187], Triterpenoid glyeosides[188], Pentacyclic triterpenes from the aerial part of the plant *Rhododendron collettianum*[189], Diterpenoids from the aerial parts of *Aconitum* leave[190].

Lappaconitine hydrobromide, revealed activity similar to that of kojic acid[191]. Crocusatin-K, isolated from the petals of *Crocus sativus*[192]

Sesquiterpenes from the leaves and stems of *Chlorantus henryi*[193]

Sesquiterpenes dimmers from the leaves of *Chloranthus tianmushanensis*[194],

Hydroxylated steroid metabolites isolated from the fungus *Cunninghamella elegans* cultivations feeding with 17⁻[ ]-ethynyl- or 17[ ]-ethylsteroids,[195]

Other Natural and Synthetic Inhibitors from Other sources:

Anthraquinones: Physcion (1,8-dihydroxy-2-methoxy-3-methylanthraquinone)[196], 1,5-dihydroxy-7-methoxy-3-methylanthraquinone[197], lignans isolated from the roots of *Vitex negundo*, most active lignan from the plant (+)-1yoniresinol[198], Phloroglueinol derivative, dieckol, isolated from a marine brown alga, *Ecklonia stolonifera*[199], marine derived fungus *Myrothecium* sp. that contain 6-n-pentyl-[ ]-pyrone[200]

*Tricoderma viride* strain H1-7, has competitive inhibition toward monophenolase activity of mushrum tyrosinase through binding to a copper active site of the enzyme.[201]

Other inhibitors from synthetic sources: N-Phenylthiourea (PTU) and its Derivatives[202-203] Synthesized N-(phenylalkyl)cinnamides derived from the coupling cinnamic acid with phenylakylamines[204], Compounds by combining the structures of two putative tyrosinase inhibitors, Kojic acid and caffeic acid[295], Analogs of cupferron[206], Nsubstituted-N-nitrusydroxylainines[217], N-hydroxybenzyl-N-nitrosohydroxylamines[208], Nsubstituted-N-nitrosohydroxylamincs[209], sildenafil[210], oxadiazole[212], oxazolones[212], tetraketones types[213], 1,3-selenazol-4-one derivatives[214], Selenourea derivatives[215], Selenium-containing carbohydrates[216], 4,4-Dihyldroxybiphenyl[217], glucoside derivatives from the fruit of *Pyracantha* fortuneana[218]

In addition to directly inhibiting tyrosinase activity, 4,4'-dihyldroxybiphenyl was also found to suppress several cellular key parameters in the melanogenic pathway by downregulating the cAMP-dependent protein kinase K signaling pathway and decreasing gene expression of microphthalmia transcription factor, which in turn suppressed tyrosinase expression[219], S-phenyl N-phenylthiocarbamate[220], 4-(2',4'-dihydroxypheny1)-(E)-3-buten-2-one.[221]

Irreversible inactivators can form irreversible covalent bond with the target enzyme and then inactivate it. They are generally specific for tyrosinase and do not inactivate all proteins, they work by specifically altering the active site of the enzyme[222], including Captopril, an antihypertensive drug [(2S)-1-(3-mercapto-2-methylpropionyl)-L-proline], forms both a copper-captopril complex and a disulfide bond between captopril and cysteinerich domains at the active site of tyrosinase[223] also as an inactivator of several copper-containing enzymes, such as dopamine 1beta-monooxygenase[224] and mushroom tyrosinase[225], Cetylpyridinium chloride[227], 3,5-dihydroxyphenyl decanoate[228], p-hydroxybenzyl alcohol showed binding capability of mushroom tyrosinase and irreversibly inhibited the enzyme[229], Hen egg white lysozyme (HEWL) inhibited mushroom tyrosinase with a reversibly and irreversibly mixed inhibition mechanism[2]"

Chemical structures of irreversible tyrosinase inhibitors:

These substrates belong to a special class. It is known that tyrosinase could be irreversibly inhibited by its o-diphenol substrates, such as L-dopa and catechol[231]. These substrates were also named suicide substrates or mechanism-based inhibitors. The mechanism of the suicide substrate has been extensively studied by Waley[232]. ,7,8.4'-trihydroxyisoflavone and 5,7.8,4'-tetrahydroxyisoflavone are potent and unique suicide substrates of mushroom tyrosinase[120], and 5,7,8,4'-tetrahydroxyisoflavone is the most potent suicide substrate of mushroom tyrosinase until now and has high potential in application as a skin-whitening agent[236].

It has been found that in humans eye color is directly dependent upon the amount of pigment granules of melanin and the amount of melanin in melanocytes of the iris stroma. For example, with little or no pigment the eye looks blue, with more pigment the eye looks green, with more pigment the eye looks hazel and even more pigment yields brown or black color.

Duplicating and greatly expediting the natural process of depigmentation of the iris requires many disparate approaches and techniques. Multiple steps of melanogenesis may need to be addressed and inhibited. This may include stopping the sympathetic or other parasympathetic nerve impulses from reaching the melanocytes, blocking the conversion of tyrosine to eumelanin, and interfering with the various means of melanin production, such as inhibiting the cyclooxigenase-2 (COX-2) enzyme and melanocyte stimulating hormone (MSH), or other biological processes. One major advantage of the iridial melanocytes is that access to the melanocytes themselves and their underlying synaptic connections is easily achieved by continuity with the fluid in the aqueous humor in the anterior compartment of the eye, since the anterior iris lacks an epithelium or basement membrane. This leaves the iridial melanoctyes bathed in and completely exposed to the aqueous humor environment.

In addition to inhibition of tyrosinase catalytic activity, other approaches to decrease iris pigmentation include denervation of melanocytes, inhibition of tyrosinase mRNA transcription, aberration of tyrosinase glycosylation and maturation, acceleration of tyrosinase degradation, interference with melanosome PH, maturation, and pigment accumulation, and inhibition of inflammation-induced melanogenic response.

In one embodiment, a method and system are described for inducing ocular hypopigmentation of the eye, in other words, decreasing or altering the pigmentation of the conjunctiva or iris, or both. The novel method involves the use of a known drug, hydroquinone that has not heretofore been known to have been used for inducing hypopigmentation in the eye, in either the conjunctiva or iris, (http://www.drugs.com/cdi/hydroquinone-creame.html; http://www.pesticideinfo.org/Detail Chemical.jsp.Recid-PC35626). The use of hydroquinone in a technique or composition non-toxic to the eye can result in making the white part of the eyes very white and lightening the otherwise darkening color of the iris during current treatment protocols for glaucoma based upon prostaglandin analogs. Whiter eyes are a desirable symbol of youthfulness and therefore highly acceptable to an aging population.

In one embodiment, a human subject is treated with 1% Memantine, 0.5% Thymoxamine, 10% Oxyresveratrol, and 2% Pilocarpine.

In another embodiment a human subject is treated with 2% Memantine, 1% Thymoxamine, 0.09% Bromfenac. and 20% Oxyresveratrol.

In yet another embodiment, a human subject is treated with 1% Memantine, 0.09% Bromfenac, 0.5% Thymoxamine, 5% H89, and 0.5% Naloxone.

In yet another embodiment, a human subject is treated with 1-Latanoprost ophthalmic solution 0.005%, 2-Forskolin eye drop 1%, and 3-Ophthalmic suspension of 1-oleoyl-2acetyl-glycerol 0.5%.

In studies of macular degeneration it has been shown that there is a significant association between light iris color, fundus pigmentation and the incidence of macular degeneration. It is known that zinc will bind to melanin in pigmented tissues and will thereby enhance antioxidant capacity as a cofactor or gene expression factor of antioxidant enzymes in the eye. This has been shown in an investigation of the uptake and storage of zinc in human irides, namely irides of blue and brown human eyes. In one study, the irides were incubated with concentrations of zinc chloride and tissue specimens were examined for the storage of zinc. It was found that the melanocytes count was significantly higher in brown tissues. No significant storage of zinc was found in blue colored irides. It was concluded that zinc uptake is dependent upon the extent of pigmentation in the iris of the human eye. Accordingly, the degree of pigmentation of a patient's eyes must be considered with respect to the effectiveness of a possible treatment for macular degeneration with a zinc supplementation. A significant aspect of this study is the conclusion that zinc uptake is more prevalent with respect to darker pigmentation or discoloration of the conjunctiva or iris of the eye. However, for the purpose of altering eye color, a delivery system using zinc to provide color-altering compositions to the conjunctiva and iris of the eye has not heretofore been realized. Similarly, with respect to altering the color of the skin and hair, there have heretofore been available only topical applications of a large variety of compositions, with limited effectiveness and longevity.

Drug delivery systems (DDS) based upon using nanoparticles to carry drugs have been known heretofore (http://www.nano.gatech.edu/about; http://web.mitedu/newsoffice/2008/nanocell-0609.html; http://www.scientistlive.com/European-Science-News"Nanotechnology/Melanoma_destroying). Nanoparticles are structures that have a large capacity for carrying drugs and can incorporate both hydrophilic and hydrophobic substances. Nanoparticles have been used as drug carriers for hydrophilic and hydrophobic substances for many years, and have been found feasible for various routes of administration. Nanoparticles are also known to allow controlled drug release over therapeutically appropriate periods of time.

There have been many instances of nanoparticle Drug Delivery Systems (DDS) that transport toxic medications safely to targeted tissue without affecting the surrounding tissue. Examples include a Tuberculosis (TB) drug delivery system[17], cancer treatment[16], and fungal infections[22]. Nanoparticles have been used to target cancer tumors or other sources of disease, such as tuberculosis. Nanoparticle-based drug-delivery systems have also demonstrated efficacy in the treatment of breast cancer. For example, tamoxifen encapsulated in polyethylene glycol molecules has been used for penetrating tumors. Inorganic nanoshells can be combined with and carry bioactive biomolecules for targeted tumor penetration and photothermal-based anticancer therapy. In one study concerning the eyes, polycyanoacrylate nanoparticles were used to improve the corneal penetration of hydrophilic drugs. A higher concentration of amikacin in the cornea and aqueous humor was found to be statistically significant over a control solution when the amikacin was placed in a nanoparticle formulation.

A nanoparticle DDS requires a specific mechanism to be targeted to the desired cell type. Zinc has been shown to have predilection to be absorbed by the melanocytes of the iris.[6] Hence, zinc can be used as a tagging agent to target melanocytes, and if the drug were administered to the eye or anterior chamber specifically, the predominate uptake would likely be by iridial melanocytes. There are many types of nanoparticles or nanoshells made of zinc itself, and others that are tagged with zinc, which can be used as a transport system for transferring the above medications directly to the melanocytes of the iris without affecting the surrounding ocular tissues.

The biomedical applications for inorganic nanoparticles are relatively recent. Inorganic nanoparticles have a metal core or a metal shell that may serve-as a substrate for joining with biomolecules. Single crystal zinc oxide has been formed into nanorings, having a uniform and perfect geometrical shape.

In one embodiment, ocular nanoparticles, for example of zinc oxide or other forms of zinc, may be combined with a pharmaceutical effective composition and concentration of hydroquinone and delivered to discolored eyes resulting from standard glaucoma treatments. Such nanoparticles which include zinc will, accordingly, target the melanocytes and bind to melanin in pigmented tissue. In such circumstances, there will be no toxic effect on surrounding eye tissue caused by the release of hydroquinone to cells defining the discolored tissues. The hydroquinone changes the amount of the pigment, for example; of the iris without any affect on the surrounding tissue. Ocular nanoparticles may be delivered to the eye in the form of eye drops, or may be delivered systemically.

Alternatively, ocular nanoparticles formed from a zinc compound may be used to deliver glaucoma medications directly to the ciliary bodies. Such a delivery system avoids both a toxic impact to eye tissue caused by hydroquinone, and avoids discoloration of the iris that would otherwise occur as a result of the application of glaucoma medication.

Proposed medicinal therapeutics can reach iridial melanocytes via topical administration to the eye with subsequent absorption into the anterior chamber, direct injection into the anterior chamber, or systemic administration, preferably with a method to enrich or target iridial melanocyte uptake. For example, botulinum toxin may also be used to block nerve transmission at synaptic level by transporting the toxin molecules safely with nanoparticle DDS (Drug Delivery System)[16-18] that is conjugated in a covalent or non-covalent manner with a targeting agent such as zinc [6-7], which is known to be preferentially taken up and stored by melanocytes. Similarly, gold nanoparticles with PEGylated anti-melanocyte antibodies have been used to treat melanoma[36], and a similar strategy could be employed here. When used in combination with tyrosinase inhibitors[8], COX-2 inhibitors,[9-11] cholinergic agonists such as Pilocarpine, and new bleaching agents such as Zinc Glycoprotein[12-13], and DMHF,[14] depigmentation of the iris may be successfully achieved. In an embodiment, oversaturating the molecule carriers can be used to overcome the inter-cellular outward flow and maximize the transport of molecules into the anterior chamber. In another embodiment, microneedles can be used to directly inject medication into the anterior chamber to bypass the superficial part of the sclera, which is infiltrated with lymphatic draining vessels (superficial ⅓rd).

In yet another embodiment, Folate receptors can also be used to carry small and large molecules inside the melanocytes. The presence of Folate Receptor-a in normal and pathological melanocytes has been identified. It has been demonstrated that Methotrexate is preferentially transported through this receptor in melanoma cells. It has also been demonstrated that cells expressing the human Folate receptor internalize a higher level of nanoparticles. (Luis Setnchez-del-Campo, Maria F. Montenegro, Juan Cabezas-Herrera and Jose Neptuno Rodriguez-Lopez, *The critical role of alpha-folate receptor in the resistance of melanoma to methotrexate", Pigment Cell Melanoma Research*, (2009) Vol. 22, No. 5, Pg 588-000).

The nanoparticles can be initially surface-modified with (3-aminopropyl) trimethoxylane to form a sell-assembled monolayer and subsequently conjugated with desired medication through amidation between the carboxylic acid end groups on the medication, and the amine groups on the particle surface. Moreover, the nanoparticles should be under low pH conditions mimicking the intracellular conditions in the lysosome for case of drug delivery. (Nathan Cohler, Conroy Sun, Jassy Wang, etal.[Langmuir 2005. 21(19)]

Since melanoma is a cancer in pigmented cells, melanoma cancer has and does occur in the eye. For example, it can occur on the iris, a ciliary body or on the choroid behind the retina. Such locations for malignant melanoma have heretofore led to a very poor prognosis for survival. Nanoparticles that contain an appropriate form of zinc can be used to target cancerous pigmented cells in or around the eye and carry anti-cancer medication that would be absorbed in the melanin of the pigmented cancer cells and therefore will affect only the pigmented cancerous cells, even if it would otherwise be toxic to normal non-pigmented cells. Normal pigmented cells would not be affected by such anti-cancer therapy when the nanoparticles are adjusted for specific cancer cell receptors.

In the case of hair, nanoparticles of a suitable form of zinc and tagged with a suitable and effective form of hydroquinone can be applied topically to the scalp: The zinc targets and binds to the melanocytes in the roots of hair follicles thereby to cause the color of the hair to change. No dying of the hair to change its color would be necessary. Because zinc binds to melanin in pigmented tissue, such nanotechnology including hydroquinone may be used systemically to affect a change in the color of hair.

Similarly, an appropriate zinc nanoparticle tagged with an effective composition and concentration of hydroquinone can be used to target and bind to melanocytes in the skin, thereby to effect an alteration in the color of the pigmented cells. The hydroquinone is carried to and will act directly on the pigmented skin cells to change the color of the skin, e.g., to make it lighter in color. Hydroquinone with nanotechnology including zinc nanoparticles to target melanocytes in the skin can be topically applied to the skin as a cream. In addition, hydroquinone with nanotechnology including zinc nanoparticles to target melanocytes in the skin can be used systemically to achieve the same results. Thus, an effective nanotechnological composition can be adjusted and delivered systemically so that the zinc element binds to melanocytes of pigmented cells in the skin and the hair, thereby to permit the hydroquinone to change the color of the skin and hair simultaneously.

Of course, malignant melanoma occurs prevalently in the pigmented cells of the skin. As indicated, a zinc nanotransfer drug delivery system can be used to treat melanoma. Nanoparticles that contain an appropriate form of Zinc, can he used to target cancerous pigmented cells in the skin and carry anti-cancer medication that would be absorbed in the melanin of the pigmented cancer cells and therefore will affect only the pigmented cancerous cells even if it would otherwise be toxic to normal non-pigmented cells. Normal pigmented cells would not be affected by such anti-cancer therapy when the nanoparticles are adjusted for specific cancer cell receptors.

The fundamental structure of hair and nails is essentially the same. Accordingly, if a zinc nanoparticle is tagged with a suitable antibiotic or anti fungal drug, the targeting of pigmented nail cells by zinc nanoparticles will deliver the drug systemically to the nail as a treatment for various nail infections.

It will be understood that using nanoparticles with targeting agents such as zinc can permit using toxic medications or toxic solutions to be safely delivered to target tissues without adversely affecting other tissues. This technique can be used to deliver very toxic medications directly and safely to target pigmented cells. In addition to zinc, other targeting agents including antibody, ligand specific targeting agents, magnetic targeting agents can also be used. Furthermore, nanoparticles can be passively transported to the target tissue and deliver the small molecules. While the foregoing description involves the use of zinc nanoparticles to carry the appropriate composition of the drug of interest, other techniques may be used without departing from the scope of the invention. For example, instead of using a zinc nanoparticle, a nanoparticle carrying hydroquinone could be tagged with a zinc composition. Moreover, any drug that affects or would alter pigmentation of tissue can be used with zinc either as a tag to a zinc nanoparticle or in the form of a nanoparticle tagged with a suitable form of zinc. Different drugs such as antibiotics or a composition of tyrosinase inhibitors can be used with zinc in various treatment protocols.

In an embodiment, a method consists of introducing to pigmented tissue a pharmaceutically acceptable toxic or non-toxic solution of hydroquinone or suitable derivative thereof Hydroquinone is a reducing agent soluble in water. Hydroquinone is known heretofore to be used as a topical application to the skin for whitening or reducing the color of skin. Hydroquinone has not been known heretofore to be used as or as part of an ophthalmic drug delivery system for the eye either in an appropriate eye drop solution or as a compositional time-release coating for inserts to the eye. Nor has hydroquinone been known to be used heretofore as a nanoparticle tagged with a suitable zinc composition nor associated with a suitable nanoparticle of zinc to bind to the melanocytes in the pigmented skin of the eye, hair, skin or nails.

In a carrier appropriate for the eye, hydroquinone will have the effect of reducing pigmentation in ocular melanocytes, as well as lightening the color of the iris, thereby reversing the darkening, effect of glaucoma medications and improving cosmetic affects and possibly assisting in the treatment of heterochromia in an appropriate eye drop solution. As indicated, a nanoparticle transport system may be used to deliver glaucoma medications directly to the ciliary bodies to avoid the darkening effect of some standard glaucoma medications.

The composition of hydroquinone by itself is known. Hydroquinone is also known as benzene-1,4-diol or quinol and is an aromatic organic compound which is a type of phenol, having the chemical formula $C_6H_4(OH)_2$. Its chemical structure has two hydroxyl groups bonded to a benzene ring in a para position. Its chemical structure is shown in a table attached hereto and incorporated by reference herein. It is a white granular solid at room temperature and pressure. In a pharmaceutically acceptable liquid solution, such as but not limited to water, hydroquinone or its suitable derivative may be introduced into the eye, in one embodiment as an eye drop.

In one embodiment, the method may consist of introducing into the eye a pharmaceutically acceptable non-toxic composition of hydroquinone in the form of a salve, cream, emulsion, gel or other solution. Since solutions, creams, emulsions or gels consisting of hydroquinone for purposes of skin-bleaching have heretofore been found to be somewhat toxic to the eyes, existing compositions or formulations including hydroquinone therefore teach away from introducing to the pigment of the eye pharmaceutically acceptable toxic and non-toxic compositions of hydroquinone for reducing pigmentation in ocular melanocytes or reducing dark color areas formed in the conjunctiva or iris as a result of many standard glaucoma medicines. Moreover, the art does not teach or suggest the use of hydroquinone with respect to nanotechnology nor in particular the combination of hydroquinone with a suitable zinc nanoparticle or hydroquinone nanoparticles tagged with zinc to target and bind to the melanocytes in pigmented body tissue for changing pigment color. Nor does the art disclose or suggest nanotransfers of medication combined with forms of zinc for treating diseases of pigmented skin, such as malignant melanoma: Nanotransfers using zinc target melanin in pigmented cells may be utilized to deliver toxic or non-toxic drug compositions to the targeted cells without adversely affecting healthy tissues.

In an embodiment, hydroquinone may be used in the eye as a component of a coated insert. Coaled inserts have been known heretofore to deliver other ophthalmic drugs (Sasaki et al., (2003) "One-side-coaled insert as a unique ophthalmic drug delivery system", Journal of Controlled Release. Vol. 92(3), pages 241-747. Some inserts coated with other ophthalmic drugs have heretofore have been one-side-coaled. It may also be possible to have an insert that is coated on two sides, depending on the drug composition used, its time-release properties and its strength. In an embodiment, a pharmaceutically acceptable non-toxic composition of hydroquinone or other small molecules may be used uniquely in connection with a one-sided coated insert. In such circumstances, the result is a time-release ocular and systemic absorption of the effective solution or composition of hydroquinone or other small molecules. This may result in higher drug concentrations in the aqueous humor and sclera, and lower drug concentrations in the plasma and conjunctiva than has been reported for the use of other drugs heretofore. The ocular and systemic absorption of a suitable hydroquinone composition or composite solution delivered by a one-sided-coated insert may be altered by the direction of insertion.

It will be understood that the nanoparticle transfer system and method described herein and based upon zinc or zinc compound nanoparticles may be used for any cosmetic or therapeutic treatment involving pigmented tissue without departing from the scope of the invention. Indeed, any kind of nanoparticle that is tagged with zinc can carry hydroquinone and/or anti-cancer medications, or depigmenting agents to the pigmented tissues. With respect to treatments for cancer, for example, see http://www.scientistlive.com/European-Science-News/Nanotechnology/Melanoma destroying nanospheres/21648/. Such articles and the others attached hereto are incorporated by reference.

Following the bleaching process of the iris as described herein, different methods of dying the eyes can be implemented to change the color of the eyes to varying hues and shades of color. This includes enhancing natural coloring such as deepening the blue or green hues, as well as unnatural colors such as purple, metallic gold or silver, or even fluorescent colors which glow in darkness or in black light (UV).

The following small molecules can be used for opposite effect, in order to darkening the color of the eye or reverse the previously lightened eye.

Topical prostaglandin (PG) F2a analogues are potent medications for managing elevated intraocular pressure (IOP). One side effect of these drugs is a darkening of iris color.(Zhan et al., 2003).

Forskolin (Naturally occurring molecule) and isobutylmethylxanthine (IBMX)(Synthetic compound) are known to regulate adenylyl cyclase and phosphodiestherases, resulting in an increase in melanin biosynthesis in melanocytes. (Brian R. et al., 200$^9$).

I-oleoyl-2-acetylglycerol, or OAG,( the naturally-occurring) and 1,2-diacylglycerol, (synthetic, or DAG). DAG's analogues and derivatives are able to induce melanin synthesis and thus produce an increase in melanin content in melanocytes. (U.S. Pat. No. 5,352,440).

Lotus (*Nelumbo nuficecra*) flower essential oil increased melanogenesis in normal human melanocytes (Songliee Jeon et al., July 2009).

The subject application describes a method of lightening the color of the iris of a human subject. In this method, a composition of a tyrosinase inhibitor is administered to the iris of a human subject in an amount effective to lighten the color of the iris.

In an embodiment of the method, the tyrosinase inhibitor is hydroquinone, Oxyresveratrol or tetrahydroxyisoflavone, preferably hydroquinone.

In another embodiment of the method, the composition can also contain at least one melanogenesis inhibitor, which are selected from the group of a glutamate receptor blocker (e.g. memantine), an a-adrenergic blocker (e.g. thymoxamine), a matrix metalloproteinases inhibitor (e.g. prinomastat), a Cox inhibitor (e.g. bromfenac), a cholinergic agonist (e.g. pilocarpine), a downregulator of mitt, tyr &Trp1 (e.g. Haginin A or 4,4'-dihyldroxybiphenyl), an acidifier of melanosomes (e.g. H89), an opioid receptor antagonist (e.g. naloxone), a Pmel 17 blocker (e.g. calmodulin inhibitors), and a fibroblast growth factor inhibitor. In particular, the composition contains hydroquinone, memantine and Haginin A; oxyresveratrol, 4,4'-dihyldroxybiphenyl and H89; or tetrahydroxyisoflavone, prinomastat and naloxone.

In yet another embodiment of the method, the composition can be administered to a human subject in conjunction with an injection of saline, siRNA, botulinum toxin, or a combination of botulinum toxin and siRNA.

The methods described herein can be administered through a nanoparticle drug delivery system containing a targeting agent of iridial melanocytes. The targeting agents include a composition of zinc, antibody, ligand specific targeting agents, magnetic targeting agents, preferably Iron a composition of zinc such as zinc oxide or Gold. The composition described herein can be in the form of eye drops or an ophthalmic drug delivery system such as salves, creams, emulsions and gels. The composition described herein can be administered in the fornices under the eyelid or as a time-release coated insert which is coated on at least one side.

The method described herein can be administered to a healthy human or a human subject afflicted with glaucoma.

The subject application also describes a method introducing pigment to the iris of a human subject. In this method, at least one melanogenesis promoter is administered to the iris of a human subject in an amount effective to introduce pigments to the iris. The iris of the human subject becomes darker idler such treatment.

In an embodiment of the method, the melanogenesis promoter includes prostaglandin, forskolin, 1-oleoyl-2-acetylglycerol and 1.2.-diacetylglycerol, and lotus flower essential oil.

The subject application further describes a method of introducing pigments to the iris of a human subject. In this method, a composition comprising a biological dye is administered to the iris of a human subject in an amount effective to introduce-pigments to-the iris. In an embodiment, the biological dye is Trypan Blue or a Methyl green biological dye.

In another embodiment of the method, the composition can also contain fluorescein. The iris of the human subject changes color and/or glows after such treatment.

In yet another embodiment of the method, the composition is administered through a nanoparticle drug delivery system containing a targeting agent of iridial melanocytes; preferably the targeting agent is a composition of zinc such as zinc oxide, Iron or Gold.

The subject application yet further describes a nanoparticle composition for lightening pigmented tissues. This nanoparticle composition contains a targeting agent of melanocytes chemically bound to a pharmaceutical composition comprising a tyrosinase inhibitor. The targeting agents include a composition of zinc, antibody, ligand specific targeting agents, magnetic targeting agents, preferably a composition of Iron zinc such as zinc oxide or Gold.

In an embodiment of the nanoparticle composition, the tyrosinase inhibitor is hydroquinone, oxyresveratrol or tetrahydroxyisoflavone, preferably hydroquinone.

In another embodiment of the nanoparticle composition, the pharmaceutical composition can also contain at least one melanogenesis inhibitor.

In yet another embodiment of the nanoparticle composition, the pigmented tissues are skin or hair tissues.

In yet another embodiment, the nanoparticle composition is in the form of an injectable solution or a topically applied solution.

The subject application yet further describes a method for lightening pigmented tissuess of a human subject. In this method, the nanoparticle composition described herein is administered to the human subject so as to lighten the pigmented tissues.

The subject application yet further describes another nanoparticle composition for treating a pigmented tissue related disease. This nanoparticle composition contains a targeting agent of melanocyte chemically bound to a pharmaceutical composition containing an active agent for the disease The targeting agents include a composition of zinc, antibody, ligand specific targeting agents, magnetic targeting agents, preferably a composition of Iron, zinc such as zinc oxide and Gold.

In an embodiment of the method, the disease is glaucoma or melanoma cancer.

The subject application yet further describes a method for treating a pigmented tissue related disease. In this method, the nanoparticle composition described herein is administered to a human subject afflicted with a pigmented tissue related disease so as to treat the disease and pigmented cancer cells such as Melanoma. It has been demonstrated that MITF Microphthalmia-associated transcription factor) is an amplified oncogene of human melanomas and that it also has an oncogenic role in human clear cell sarcoma. MITF is a major contributor of pigment formation in both healthy and cancerous pigmented cells. For these reasons downregulation of the MITF can be applied to both healthy pigmented cells to change the color of the tissue, or to the cancer cells to stop the growth of the tumor.

In the methods described herein, the targeting agent binds to cells of the pigmented tissues to permit the release of the pharmaceutical composition directly into the cells of the pigmented tissue without affecting non-pigmented cells.

The subject application yet further describes a method of depigmenting the iris melanocytes to lighten the color of the iris. This method includes the use of one or more of the following steps:

Blocking the sympathetic and parasympathetic nerve supply to the melanocytes using botulinum toxin and memantine;
Preventing tyrosine conversion to melanin by one of available tyrosinase inhibitors;
Preventing Melanocyte-stimulating hormone activation (MSH) by using 2,5-Dimethyl-4-hydroxy-3(2H)-furanone (DMHF);
Inhibiting the COX-2 enzyme using NSAIDS;
Preventing melanogenesis by using a cholinergic agonist;
Blocking Alpha 1-adrenergic receptors by using antagonist chemicals;
Transcriptional regulation of Melanogenic Enzymes by downregulation of MITF by Transforming Growth Factor (TGF) Beta Family; and
Post-Transcriptional Modification of Melanogenic Enzymes by Inhibiting Nglycolysation of melanosomal enzymes.

As used herein, a melanogenesis inhibitor refers to a compound that inhibits any step of melanogenesis. For example, a melanogenesis inhibitor inhibits conversion from Dopaquinone to 5-S-Cysteinyldopa; conversion from 5-S-Cysteinyledopa to 5-S-Cysteinyklopa, conversion from 5-S-Cysteinyklopa to Benxothiazine intermediaries, conversion from Benxothiazine intermediaries to Pheomelanin, conversion from 5-S-Cysteinyklopa to Pheomelanin, conversion from 5-S-Cysteinyklopa to Pheomelanin, conversion from Dopaquinone to Leucodopachrome, conversion from Dopaquinone to Eumelanin, conversion from Leucodopachrome to Eumelanin, conversion from Leucodopachrome to Dopachrome, conversion from Leucodopachrome to Dopachrome, conversion from Dopachrome to Eumelanin, conversion from Dopachrome to 5,6- Dihydroxyindole-2-carboxylic acid, conversion from Dopachrome to 5,6-Dihydroxyindole, conversion from 5,6-Dihydroxyindole-2-carboxylic acid to Eumelanin, conversion from 5,6-Dihydroxyindole to Eumelanin, conversion from 5,6-Dihydroxyindole to Indole-5,6-quinonecarboxylic acid, or conversion from Indole-5,6-quinone to Eumelanin. A melanogenesis inhibitor also optionally includes Tyrosinase inhibitors, which inhibit conversion from Tyrosine to Dopa or from Dopa to Tyrosinase.

As used herein, a melanogenesis promoter refers to a compound that activates any step of melanogenesis. For example, a melanogenesis promoter activates conversion from Dopaquinone to 5-S-Cysteinyldopa; conversion from 5-S-Cysteinyldopa to 5-SCysteinyklopa, conversion from 5-S-Cysteinyklopa to Benxothiazine intermediaries, conversion from Benxothiazine intermediaries to Pheomelanin, conversion from 5-SCysteinyklopa to Pheomelanin, conversion from 5-S-Cysteinyklopa to Pheomelanin, conversion from Dopaquinone to Leucodopachrome, conversion from Dopaquinone to Eumelanin, conversion from Leucodopachrome to Eumelanin, conversion from Leucodopachrome to Dopachrome, conversion from Leucodopachrome to Dopachrome, conversion from Dopachrome to Eumelanin, conversion from Dopachrome to 5,6-Dihydroxyindole-2-carboxylic acid, conversion from Dopachrome to 5,6-Dihydroxyindole, conversion from 5,6-Dihydroxyindole-2-carboxylic acid to Eumelanin, conversion from 5,6-Dihydroxyindole to Eumelanin, conversion from 5,6-Dihydroxyindole to Indole-5,6-quinonecarboxylic acid, or conversion from Indole-5,6-quinone to Eumelanin. A melanogenesis promoter also activates conversion from Tyrosine to Dopa or from Dopa to Tyrosinase.

As used herein, a targeting agent of a certain cell type (e.g. melanocytes) refers to an agent (e.g. a molecule or a composition of a molecule), which is preferential taken up and stored by the cell type.

As used herein, a targeting agent "chemically bound" to a pharmaceutical agent refers to the targeting agent is conjugated with the pharmaceutical agent in a covalent or non-covalent manner.

As used herein, a pigmented tissue related disease refers to a disease in which diseased cells reside in pigmented tissues or tissues that contains pigment molecules (Melanin).

This invention will be better understood from the experimental details that follow. However, one skilled in the art will readily appreciate that the specific methods and results discussed are merely illustrative of the invention as described more fully in the claims that follow thereafter.

EXPERIMENTAL DETAILS

Bleaching
Active Agents
The following list contains a partial list of drugs can be tested for use in bleaching and/or coloring.
Tyrosinase inhibitor*
Glutamate receptor blocker (Memantine)(CAS)
Adrenergic blocker (Thymoxamine)(CAS)
Cox inhibitor (Bromfenac)*
Cholinergic agonist (Pilocarpine)(CAO)
Downregulator of mitf, tyr & Trp1 (Haginin A)(CAD)*
Acidifier of melanosomes (H89)*
Matrix metalloproteinases inhibitor (prinomastat)
Opioid receptor antagonist (Naloxone)*
Pmel 17 blocker (Calmodulin inhibitors)*
MITF downregulation (by TGF beta family such as TGF-beta-1 & TGF beta-2)
Post-Translational Modification of Melanogenic Enzymes (N-Glycosylation Inhibitors)
Fibroblast growth factor inhibitor*
siRNA gene silencing Various combinations of the drugs are tested using cell culture in vitro (*) and the most effective combinations are chosen for animal studies.

In animal studies, the most effective combinations from in vitro studies are used in conjunction with various combinations of the remaining therapies (those not marked with *).

Transport System
The following is a list of methods that can be used to deliver to the iris of any one or any combination of the above listed small molecules.
Topical (A. S. Mundada, PharmaInfo.net, Vol. 6, Issue I, 2008)

Conventional
Ointments
Solutions
Suspensions
Gels
Emulsions
Inserts (erodible and non-erodible)
Recent
Penetration Enhancers
Mucoadhesive Polymers
In Situ gelling systems
Colloidal systems
Iontophorosis
Nanoparticles (e.g. Fullerenes and Carbon Nanotubes, Liposomes, Nanoshells, Dendrimers, Superparamagnetic Nanoparticles. Nanorods, Quantum Dots)
Injectable (subconjunctival, subtenon, into the anterior chamber, intravitreal. intravenous)
Solutions
Suspensions
Gels
Emulsions
Inserts
Nanoparticles
Targeting and Vehicles The following is a sampling of targeting mechanisms and vehicles used that could be used to deliver to specific target cells or organelles, i.e. melanocytes or melanosomes via topical eye drops or microneedle injection. Once the vehicle is delivered to the destination, it can be released through various means, such as photodynamic therapy (PDT) (Drug Discov. Today. 2008 February; 13(3-4): 12/1 134), pH sensitive drug delivery (Journal of Controlled Release, Volume 103, Issue 1, 2 March 2005, Pages 137-148), and thermally sensitive drug delivery (K. S. Soppimath, D. C.-W. Tan, Y.-Y. Yang, pH-Triggered Thermally Responsive Polymer Core-Shell Nanoparticles for Drug Delivery, Volume 17 Issue 3, Pages 318 - 323) or laser activated nanoparticles (Dimitri Laptco et al, Cancer letters 2006)

Containers
Positively Charged Dendrimers
Positively charged Dendrimers cause membrane defects, which leak cellular proteins and through which particles can pass.

Liposomes
"Liposomes are microscopic and submicroscopic vesicles with sizes ranging from 10 nm to 20 um. They are usually made up of phospholipids, although other amphiphiles such as nonionic surfactants can also be employed for their construction. When phospholipids are hydrated, they spontaneously form spherical lipid bilayers enclosing the aqueous medium and the solute. Liposomes offer several advantages over other delivery systems including biocompatibility, control of biological properties via modification of physical properties e.g., lipid composition vesicle size, lipid membrane fluidity etc.) and several modes for drug delivery to cells (e.g., absorption, fusion, endocytosis, phagocytosis). Liposomes can be classified according to the number of the lipid bilayers as unilamellar vesicles (ULVs) and multilamellar vesicles (MLVs). Functionalized liposomes can be synthesized using peptides and oligosaccharides in order to achieve both targeting and circulation longevity. Peptides can be used in order to guide liposomes to desired receptors whereas, poly (ethylene oxide) (PEO)-grafted phospholipids are known to dramatically increase liposome survival in the circulation. A surface modified liposomal drug delivery vehicle can be developed for selective targeting by coupling an argentine-glycine-aspartic acid (RGD) peptide to the liposome through a PEO spacer.[49]

Cell Penetrating Peptides
Cell penetrating peptides are short peptides that facilitate cellular uptake of molecular cargo from small molecules to nanoparticles and large DNA fragments. "Various in vitro and in vivo studies have proved the potential of cell-penetrating peptides (CPPs), including TAT peptide (TATp) and oligoarginines, for the intracellular delivery of different cargoes. TATp-mediated cytoplasmic uptake of polymers (Nori et al. 2003; Hyndman et al. 2004), bacteriophages (Paschke et al. 2005), plasmid DNA (Torchilin et al. 2001, 2003; Kleemann et al. 2005), magnetic nanoparticles (Dodd et al. 2001; Zhao et al. 2002; Nitin et al. 2004), liposomes (Cryan et al. 2006; Sawant et al. 2006; Gupta et al. 2007), and micelles (Sawant et al. 2006; Sethuraman et al. 2007/2008) has been reported. Successful intracellular delivery requires direct contact between the surface-attached CPPs on the pharmaceutical nanocarrier and the cell surface" (Torchilin et al. 2001; Levchenko et al. 2003

Receptor-Mediated Endocytosis
Receptor-mediated Endocytosis is a process by which cells internalize molecules by the inward budding of plasma membrane vesicles containing proteins with receptor sites which specifically bind to the molecules being internalized. (*Nature Reviews Molecular Cell Biology* 6,112-126 (February 2005)1 doi:10.1038/nrm1571)

Targeting Agent
Zinc
The high concentration of Zn (II) ion inside the melanosomes may create a good target for a transport system utilizing zinc fingers (ligands) to deliver a payload of drugs specifically to the melanosomes.

"Zinc is a feature trace element of pigment cells and tissues. Organelles, in which melanin is synthesized and stored, i.e. melanosomes, represent a zinc reservoir at the subcellular level. In order to understand function of metals in tissues, cells and their constituents, knowledge is needed on metal interactions with intracellular targets. The possible zinc ligands in pigment cells include melanin, metallothionein, melanotransferrin, B700 and related proteins, ferritin, zinc enzymes and low molecular weight ligands. Areas of a special interest in relation of pigment cells and structures to zinc—such as zinc effect on melanogenesis, zinc excretion and buffering by melanosomes, zinc function in free radical processes as well as zinc role in melanomas—have been reviewed. High level of zinc in pigment cells may indicate a physiological defense against the potential danger of oxidative stress.[50]

Antibodies
Antibodies to Melanin can be used to specifically target Melanosomes. Antibodies currently under investigation or in use include melanin-binding IgM antibody from Goodwin Biotechnology Inc., murine monoclonal antibodies[51], and monoclonal antibody 6D2[52].

Depending on the drug to be delivered, different methods can be Used to associate the drug with the antibody, such as Polymer (H1)[53-54], Liposome[55], and Dendrimers[55]

Coloring and Texturing

Using the transport and targeting systems described herein, pigments and/or dyes (including fluorescent, metallic, and other dyes and pigments) or other chemicals are introduced, to change directly or indirectly the appearance of the iris.

If the natural color of the eye does not permit the desired change, then bleaching step as described herein may be done prior to or in conjunction with the texturing and coloring.

Targeting

Unlike in Bleaching step described herein, our targets are expanded to include connective tissue or the anterior surface of the iris, including collagen[5], fibroblasts, interstitial matrix, and vascular tissue. The targeting mechanism has very high specificity for the above targets in order to prevent unwanted color change of the other parts of the eye including the cornea and the lens. This is achieved through selection of the appropriate antibodies, collagen adhesives (U.S. Pat. No. 5,219, 895), and tissue adhesives[58].

Containers

Common biological stains and/or Fluorescent materials such as Fluorescein sodium dye are encapsulated in nanoparticles such as liposomes as described herein, and targeted with mechanisms explained above.

Standard techniques for loading the dye cargo into the liposomes can be used

Example 1

Cell Cultures

Typical cell culture methods and measurement of tyrosinase activity and statistical analysis may be employed, as described in Yeon Mi Kin et al[66].

Culture of Murine Melanoma B-16

The cells can be grown in DMEM (13.4 mg/ml Dulbecco's modified Eagle's medium, 24 mM NaHCO3, 10 mM HEPES, 143 units/ml penicillin G potassium, 100 µg/ml streptomycin sulfate, pH 7.1) containing 10% FBS with 5% $CO_2$ at 37° C. When the cells are confluent, PBS buffer (0.2 M NaCl, 2.7 mM KCl, 10 mM NaH2PO4, 1.8 mM K2HPO4) containing 0.25% trypsin and 0.02% EDTA can be added to detach the melanoma cells from a culture dish. The detached cell suspension can be 10-fold diluted with DMEM containing 10% FBS and then centrifuged at 250×g for 10 min at 4° C. After washing with DMEM twice, melanoma cells can be resuspended in DMEM containing 10% FBS, and their numbers counted by using a microscope to check the viability of the melanoma cells. The cells can be diluted to 2×105 cells/culture dish (100 mm in diameter) for passage and then incubated with 5% $CO_2$ at 37° C. for 3 days.

Culture of Normal Human Iris Stromal Melanocytes

The cells from the anterior surface of the iris will be dissected from a fresh donor eye from the Eye Bank. The processing and harvesting techniques are as in standard-mariner as described in Journal of Cellular Physiology (Mark R. Pittlecow et al 2005) and the above details.

Measurement of Tyrosinase Activity

L-Tyrosine oxidation by tyrosinase is spectrophotometrically determined.[1-2] Forty microliters of 25 mM L-tyrosine, 80 id of 67 mM sodium phosphate buffer (pH 6.8), and 40 ul of the same buffer with or without test sample are added to a 96-well plate, and then 40 of tyrosinase is mixed. The initial rate of dopachrome formation from the reaction mixture is determined as the increase of absorbance at wavelength 492 nm per min (AA 492/min) by using a Molecular Devices microplate reader. The Michaelis-Menten constant (K m) and maximal velocity (V max) of tyrosinase are determined by Lineweaver-Burk plot with various concentrations of L-tyrosine as a substrate.

Measurement of Promoter Activity of Murine Tyrosinase Gene

Murine Melanoma B-16 cells (6×104) transfected with luciferase expression vector pGL2 containing the full-length promoter of murine tyrosinase is grown in DMEM containing 10% FBS with 5% $CO_2$ at 37° C. for 24 h. After washing with PBS buffer, the cells are incubated with or without test sample for 6 h before harvesting. Luciferase activity in cell lysates is determined using a luciferase assay system (Promega) following the supplier's instructions. The light intensity is measured with a luminometer. Protein concentration is determined by the Bradford method with bovine serum albumin as a standard.

Statistics

Effects on tyrosinase by test samples are represented as inhibition % of {1-((sample deltaA 492/min))/(control deltaA 492/min))}×100 or control % of ((sample deltaA 492/min)/(control deltaA 492/min))×100. Data shall be collected as means±S.E. of three independent tests, and significant differences from the control is analyzed by the Student's t-test.

Procedures and Results

The effects of different chemical compounds are investigated using cell suspensions of uveal melanocytes and culture of murine melanoma cells, B16-FI and/or NHIMC. The cells are treated with different concentrations of specific medications and compounds described above for 72 h. Extracellular melanin is measured directly by collecting the tissue culture supernatants and taking absorbance at 490 nm. The melanin content can be measured using any of the previously reported methods (Tadokoro, T, et al, J. Invest. Dermatol. 124,1326-1332). Briefly, the cultured cells are solubilized in lysis buffer (1% Nonidet P-40; Calbiochem, San Diego, Calif., USA; in PBS containing a protease inhibitor cocktail; Roche, Indianapolis, Ind., USA) for 1 h on ice with occasional vortexing, and protein concentrations is measured with a bicinconinic acid kit (Pierce, Rockford, Ill., USA). Melanin pellets were dissolved by incubation in NaOH at 37° C. for 18 h. Aliquots of each sample were transferred to 96-well plates, quantitated by absorbance at 405 nm using an automatic microplate reader (Molecular Devices, Sunnyvale, Calif., USA), and calibrated against a standard curve generated using synthetic melanin (Sigma, St. Louis, Mo., USA).

Viability of cells is measured using standard tetrazolium reduction assays that are based on redox potential of live cells. Treatment of cultured above mentioned melanocytes with designated medications for up to 6 d can reveal any cytotoxicity.(Terry L. Riss, Richard A. Moravec. ASSAY and Drug Development Technologies. February 2004, 2(1): 51-62. doi:10.1089/154065804322966315).

Results from tyrosinase activity, promoters activity and cell viability of tyrosinase inhibitors and all the categories that has been described above, can be obtained in order to process the necessary steps to choose the best combination for the animal study.

Example 2

Animal Study

Wild caught young adult female cynomolgus monkeys of any ages, weighing 2-3 kg, can be used for the study. Typically these animals have yellowish-orange iris color, with individual-to-individual differences in hue. The animals chosen shall have no detectable heterochromia between the eyes at baseline. The animals are euthanized after 25 or 38 weeks of treatment with a mixture of pentobarbital and ethanol, and the eyes are enucleated. The eyes are opened and the irides carefully excised, washed with PBS, and placed with the pigment epithelial side up in PBS on tissue paper. The pigment epithelium is carefully removed, rinsed in PBS, and wet weight determined. The tissue is kept frozen until analyzed for melanin.

The comparison of the treated and not treated eye of each individual animal is evaluated and documented to obtain the best combination possible for human study selection.

Prior to euthanasia, color photographs of the iris of both eyes of each animal (1:1 magnification) are taken at baseline, and at regular intervals thereafter through 6 weeks, using a calibrated digital color camera system. Photographs are of each eye with a calibration plate and an animal identifier repeated every week. After color correction based on the calibration plates, the histograms of the iris portion of the photos are recorded, to be compared to reveal color shifts using peak detection in the hue and luminance histograms.

Determining the minimum shift required to qualify for a significant iris color change is done independent of the above, and can be done by the following method.

A set of 50 headshots of different people with different eye colors obtained. 20 human subjects are shown each photo, immediately followed by the same photo manipulated using editing software to shift the peaks of the hue and luminance of the iris by a random amount. The subject is then asked if they notice what they would consider a significant color change in the eyes. The average of all responses is used to determine the threshold.

Analysis of the type and level of melanin in the stroma of treated and untreated control irides is achieved by a highly sensitive procedure based on alkaline hydrogen peroxide degradation, or reductive hydrolysis with hydriodic acid of the tissue, followed by HPLC quantitation of 2,3,5-pyrroletricarboxylic acid (PTCA), and isomeric aminohydroxyphenylalanines (AHPs), the specific structural markers of eumelanin and pheomelanin, respectively (GIUSEPPE PROTAI, et al., PIGMENT CELL RES 13: 147-150. 2000)

Tyrosinase activity and statistical analysis of the results is then performed as described above.

Example 3

Bleaching

Example 3A

A suspension with a combination of the following medication is used in this example.
Hydroquinone (Benzene-1,4-diol Tyrosinase inhibitor)
Liposomes and/or micelle nanoparticles with Hydroquinone loaded multilamellar vesicles (MLVs) that are encapsulated in poly-lactic-coglycolic acid (PLGA) microparticles Memantine (1-amino-3,5-dimethyl-adaniantane glutamate receptor blocker) Haginin A (an isoflav-3-ene; downregulator of mitf, tyr, and Trp1)

The following four groups of animals are studied:
Group 1: one drop of the formulation above, twice a day (always in the right eye, with the left eye being the control), in conjunction with an injection of saline.
Group 2: one drop of the formulation above, twice a day (always in the right eye, with the left eye being the control), in conjunction with an injection of siRNA.
Group 3: one drop of the formulation above, twice a day(always in the right eye, with the left eye being the control), in conjunction with an injection of botulinum toxin.
Group 4: one drop of the formulation above, twice a day (always in the right eye, with the left eye being the control), in conjunction with an injection of botulinum toxin and siRNA.

The left eye will be the control for the drops in Group 1, and Group 1 (with saline injection) will be the control group for the injections. We then select the best result.

The change in the color of the treated right eye within 2 weeks of starting the treatment is observed. The decrease pigmentation appears as a lighter color eye compared to the untreated left eye. By the end of 3 months of treatment significant-color change is observed. At this point the maintenance therapy can be initiated.

Example 3B

A suspension with a combination of the following medication is used in this example.

Oxyresveratrol (Tyrosinase inhibitor)

4,4'-dihyldroxybiphenyl (downregulator of cAMP-dependent protein kinase K and mitf)

H89 (Melanosome acidification)

The following four groups of animals are studied:

Group 1: one drop of the formulation above, twice a day (always in the right eye, with the left eye being the control), in conjunction with an injection of saline.

Group 2: one drop of the formulation above, twice a day (always in the right eye, with the left eye being the control), in conjunction with ah injection of siRNA.

Group 3: One drop of the formulation above, twice a day (always in the right eye, with the left eye being the control), in conjunction with an injection of botulinum toxin.

Group one drop of the formulation above, twice a day (always in the right eye, with the left eye being the control), in conjunction with an injection of botulinum toxin and siRNA.

The left eye will be the control for the drops in Group 1, and Group 1 (with saline injection) will be the control group for the injections. We then select the best result.

The change in the color of the treated right eye within 2 weeks of starting the treatment is observed. The decrease pigmentation appears as a lighter color eye compared to the untreated left eye. By the end of 3 months of treatment significant color change is observed. At this point the maintenance therapy can be initiated.

Example 3C

A suspension with a combination of the following medication is used in this example.

Tetrahydroxyisoflavone (Suicide substrate)

Prinomastat (matrix metalloproteinases inhibitor)

Naloxone (Opioid receptor antagonist)

The following four groups of animals are studied:

Group 1: one drop of the formulation above, twice a day (always in the right eye, with the left eye being the control), in conjunction with an injection of saline.

Group 2: one drop of the formulation above, twice a day (always in the right eye, with the left eye being the control), in conjunction with an injection of siRNA.

Group 3: one drop of the formulation above, twice a day (always in the right eye, with the left eye being the control), in conjunction with an injection of botulinum toxin.

Group 4: one drop of the formulation above, twice a day (always in the right eye, with the left eye being the control), in conjunction with an injection of botulinum toxin and siRNA.

The left eye will be the control for the drops in Group 1, and Group 1 (with saline injection) will be the control group for the injections. We then select the best result.

The change in the color of the treated right eye within 2 weeks of starting the treatment is observed. The decrease pigmentation appears as a lighter color eye compared to the untreated left eye. By the end of 3 months of treatment maximum color change is observed. At this point the maintenance therapy can be initiated.

Example 3D

A thirty three year old female patient presents with heterochromia due to Homer's syndrome, complaining of differing eye colors. The darker eye is treated with eye drops containing 1% Memantine, 0.5% Thymoxamine, 10% Oxyresveratrol, and 2% Pilocarpine, one drop twice a day. In addition, injections of nanoparticle targeted botulinum toxin every three months are given using microneedles. Over time the darker eye lightens to resolve heterochromia. Maintenance drug therapy will continue, one drop twice a day, twice a week. The heterochromia does not redevelop.

Example 3E

A fifty seven year old male patient presents with glaucoma in one eye, complaining of disparity of eye color due to use of prostaglandin analog for treatment of glaucoma. The darker eye is treated with eye drops containing 2% Memantine, 1% Thymoxamine, .09% Bromfenac, and 20% Oxyresveratrol. Over time the darker eye lightens to resolve the disparity in eye color. The patient will have to continue the treatment as long as they are using prostaglandin analog.

Example 3F

A thirty-year-old female presents in the office with the request for lighter color eyes for cosmetic reasons. She mentions that all her life she wishes she had light colored eyes. A complete ophthalmological exam reveals no evidence of pathology or disease. She is informed of her options such as colored contact lenses and implants, and selects treatment using the following iris lightening technique. She is treated with eye drops containing 1% Memantine, 0.09% Bromfenac, 0.5% Thymoxamine, 5% H89, and 0.5% Naloxone, one drop, twice a day. In addition, injections of nanoparticle targeted botulinum toxin every three months are given using microneedles.

Example 3G

A 24-year-old female with brown eyes presents in the office explains as one of two identical twins she wishes to have her own separate identity, and as such desires lighter colored eyes. The ophthalmological examination reveals no evidence of pathology or disease. He is treated with the same formulation as in Example 3F with similar results.

Example 4

Coloring and Texturing

Trypan Blue biological dye (500 nm wavelength absorption) is encapsulated in liposomes using procedure described above. The resulting liposomes are put in two batches, each batch targeting a different iris structure.

The first batch of liposomes is conjugated with a specific antibody to collagen type VI, using the referenced method in Targeting Agent sample described herein.[55]

The second batch of liposomes is conjugated with Fibroblast Surface Protein (human) antibody"[63-64]. The two batches are then mixed into a single mixture to be used.

A 50:50 mixture of Methyl Green (560 nm+wavelength absorption) and Fluorescein is encapsulated in liposomes using procedure explained in example 1 above, to be used to generate a glowing green color when exposed to black light, or a deeper green under normal light.

Example 4A

A 42-year-old male with blue eyes presents in the office with the desire to change his appearance as part of the Witness Relocation Program. The ophthalmological examination revealed no evidence of pathology or disease. He is treated with a melanocyte stimulatory formulation resulting darkening of the eye to brown color.

Example 4B

A 23-year-old female with green eyes presents in the office, requesting Fluorescein glow in her eyes due to her profession as a hostess in a nightclub. The ophthalmological examination revealed no evidence of pathology or disease. She is treated with Fluorescein filled liposome formulation as described above. After treatment her iris began to glow under black light.

Example 4C

A 35-year-old female with light green eyes, presents in the office requesting to change her eye colors to dark brown. Initial complete ophthalmologic examination reveals no evidence of ocular pathology. She is treated with topical solutions of:

Latanoprost commercially available ophthalmic solution 0.005% (50 ug/mL), one drop per day in each eye.

Forskolin Commercially available eye drop 1%, also one drop once a day in each eye.

Ophthalmic suspension of (1-oleoyl-2-acetyl-glycerol 0.5 %), one drop twice a day until the desired color is achieved.

The color of the eye starts to darken by the first week of treatment and probably is not reversible. The treatment can be repeated in 3 months if further color darkening is desired.

Example 4D

A 43 year old male who has been treated, with bleaching eye color treatment 2 years ago, presents to the office requesting to change the color of his eyes back to original dark brown.

Initial complete ophthalmologic examination reveals no evidence of ocular pathology. He is treated with topical solutions of:

Latanoprost commercially ophthalmic solution 0.005% (50 ug/mL), one drop per day in each eye.
Forskolin Commercially available eye drop 1%, also one drop once a day in each eye.
Ophthalmic suspension of (1-oleoyl-2-acetyl-glycerol 0.5 %), one drop twice a day until the desired color is achieved.

The color of the eye starts to darken by the first week of treatment and probably is not reversible. The treatment can be repeated in 3 months if further color darkening is desired.

Example 4F

A 34-year-old male suffering from complications of iris color implant which has resulted in secondary surgical removal of the implants, presents to the office requesting iris color lightening treatment. He is treated with PEGylated liposomes containing TGF-beta complex with surface targeting coated specifically for the melanosomes using microneedle delivery via partial thickness in the Sclera. The treatment continues every 3 months until the desired color shade is achieved.

CONCLUSION

The results from above examples show that use of the methods described herein effectively changes the amount of pigment melanin in the iris stroma, and/or introduce pigments or dyes, including fluorescent or metallic, thereby altering the appearance of the iris. The subject matter of each of the references listed below is incorporated in this application by reference.

CITATIONS

Hu D N, Woodward D F, McCormic S A. Influence of Autonomic Neurotransmitters of Human Uveal Melanocytes in vitro. Experimental Eye Research, Vol. 71, Issue 3, September 2000, pp. 217-224
Mukuno K, Witmer R. Innervation of melanocytes in human iris. Graefe's Archive for Clinical and Experimental Ophthalmology, Vol. 203, Number 1/March, 1977
Dryja T P, Albert D M. Lack of Adrenergic Influence on the Pigmentation of Iris Nevus Cells. Archives of Ophthalmology, Vol. 98 No. 11, pp. 1902-2098 November 1980
Laties A M, Lerner A B. Iris colour and relationship of tyrosinase activity to adrenergic innervation. Nature, 255, 152-153 (8 May 1975)
McCartney A C E, Riordan-Eva P, Howes R C, Spalton D J. Horner's syndrome: an electron microscopic study of a human iris. British Journal of Ophthalmology 1992; 76: 746-749
Kokkinou D, Kasper H U, Bartz-Schmidt K U, Schraermeyer U. The Pigmentation of Human Iris Influences the Uptake and Storing of Zinc Pigment Cell Research, Vol. 17, Issue 5, pp. 515-518
Shameer P, Prasad P V, Kaviarasan P K. Serum zinc level in vitiligo: A case control study. IndianJ Dermatol Venereol Leprol 2005;71:206-7
Guyonneau L, Murisier F, Rossier A, Moulin A, Beermann F. Melanocytes and Pigmentation are Affected in Dopachrome Tautomerase Knockout Mice. Molecular and Cellular Biology, April 2004, pp. 3396-3403, Vol. 24, No. 8
Damm J, Rau T, Maihofner C, Pahi A, Brune K. Constitutive Expression and Localization of COX-1 and COX-2 in Rabbit Iris and Ciliary Body. Experimental Eye Research, Vol. 72, Issue 6, June 2001, pp. 611-621
Wentzel P, Bergh K, Wallin O, Niemela P, Stjernschantz J. Transcription of Prostanoid Receptor Genes and Cyclooxygenase Enzyme Genes in Cultivated Human Iridial Melanocytes from Eyes of Different Colours. Pigment Cell Research, Vol. 16, Issue 1, pp. 43-49
Rys-Sikora K E, Konger R L, Schoggins J W, Malaviya R, Pentland A P. Coordinate expression of secretory phospholipase A2 and cyclooxygenase-2 in activated human keratinocytes. American Journal of Physiology—Cell Physiology, Vol. 278, Issue 4, C822- C833, April 2000
Hale P L. Zinc alpha-2-glycoprotein Regulates Melanin Production by Normal and Malignant Melanocytes. Journal of Investigative Dermatology (2002) 119, 464-470 Ochiai Y, Kaburagi S, Okano Masaki H, Ichihashi M, Fuhasaka V. Sakurai H. A Zn(11)-glycine complex suppresses UVB-induced melanin production by stimulating metallothionein expression. International Journal of Cosmetic Science, Vol. 30, Issue 2, pp. 105-112
Lee J, Jung E, Lee J, Huh S, Boo Y C, Hyun C G, Kim Y S, Park D. Mechanisms of melanogenesis inhibition by 2,5-dimethyl-4-hydroxy-3(2H)-furanone. British Journal of Dermatology, 2007 August; 157(2): 242-8
Vince/xi F F. Effects of Botulinum Toxin on Autonomic Nerves in a Dully Innervated Tissue. Nature 213, 394-395
Kumar M N V R. Nano and Microparticles as Controlled Drug: Delivery Devices. Journal of Pharmacy & Pharmaceutical Sciences 3(2): 234-258, 2000
Gelperina S. Kisich K, Iseman M D; Heifets L. The Potential Advantages o Nanoparticle Drug Delivery Systems in Chemotherapy of Tuberculosis. American Journal of Respiratory and Critical Care Medicine Vol 172. pp. 1487-1490, (2005)
Moreau J W, Weber P K, Martin M C, Gilbert B, Hutcheon I D, Banfield J F. Extracellular Proteins Limit the Dispersal of Biogenic Nanoparticles. Science 15 June 2007: Vol. 316, No. 5831, pp. 1600 -1603
Bell M S, Vermeulen L C, Sperling K B. Pharmacotherapy With Botulinum Toxin: Harnessing Nature's Most Potent Neurotoxin. Pharmacotherapy, 2000 September; 20(9): 1079-91
Carruthers A, Carruthers J. Botulinum Toxin Products Overview. Skin Therapy Letter, Volume 13, Number 6, July-August 2008
Haider R M, Richards G M. Topical Agents Used in the Management of Hyperpigmentation. Skin Therapy Letter, Volume 9, Number 6, June-July 2004
Shahi S K, Patra M. Microbially Synthesized Bioactive Nanoparticles and their Formulation Active Against Human Pathogenic Fungi. Reviews on Advanced Materials Science 5(2003) 501-509
First E R, US Patent Number 20050220734 Therapy for Melanin Related Afflications
First E R, US Patent Numbers 20080199498 20090087459 Methods for Treating Eye Disorders
Lloyd T, Kochel R L, Weinstein J M. The effect of sympathectomy upon iris tyrosinase activity. Vision Research, 1985;25(2):213-7
Rowland L P. Stroke, Spasticity, and Botulinum Toxin. New England Journal of Medicine 2002; 347:382-383

Damm J, Rau 'f,: Maihofner C, Pahl A, Brune K. Constitutive expression and localization of COX-1 and COX-2 in rabbit iris and ciliary body. Experimental-Eye Research 2001, Vol. 72, No. 6, pp. 611-621

Robert T. Lyons, Hongwen Ma. John T. Trogden, US Patent 2004/0170665 Methods, Compositions and Drug Delivery System for Interocular Delivery of siRNA Molecules.

First E R, US Patent 2008/0014159 Methods for treating melanin related afflictions by local administration of a Clostridial toxin, such as a botulinum toxin, to a patient with a melanin related affliction.

Chawla S, deLong M A, Visscher M O, Wickett R R, Manga P, Boissy R E, Mechanism of tyrosinase inhibition by deoxyArbutin and its second-generation derivatives, British Journal of Dermatology, 2008 December; 159(6):1267-74.

Yeon Mi Kim, Jieun Yun, Chong-Kil Lee, Hwanghee Lee, Kyung Rak Min, Youngsoo Kim, Oxyresveratrol and Hydroxystilbene Compounds, JBC 2002, Feb. 25, 2002, doi: 10.1074/jbc.M200678200

Jin Hee Kim, Seung Hwa Baek, Dong Hyun Kim, Tae Young Choi, Tae Jin Yoon, Jae Sung Hwang, Mee Ree Kim, Ho Jeong Kwon, Choong Hwan Lee, Downregulation of Melanin Synthesis by Haginin A and Its Application to In Vivo Lightening Model, Journal of Investigative Dermatology (2008) 128,1227-1235

Ancans Janis, Tobin Desmond J., Hoogduijn Martin J., Smit Nico P., Wakamatsu Kazumasa, Thody Anthony J., Melanosomal pH Controls Rate of Melanogenesis, Eumelanin/Phaeomelanin Ratio and Melanosome Maturation in Melanocytes and Melanoma Cells, doi: 10.1006/excr.2001.5251

Ancans Janis, Tobin Desmond J., Hoogduijn Martin J., Smit Nico P., Wakamatsu Kazumasa, Thody Anthony J., Melanosomal pH Controls Rate of Melanogenesis, Eumelanin/Phaeomelanin Ratio and Melanosome Maturation in Melanocytes and Melanoma Cells Kuliawat R, Santambrogio L., A mutation within the transmembrane domain of melanosomal protein Silver (Pme117) changes lumenal fragment interactions. Eur J Cell Biol. 2009 November; 88(11):653-67.

Wei Lu, Chiyi Xiong, Guodong Zhang, Qian Huang, Rui Zhang/Jin Z. Zhang, Chun Li, Targeted Photothermal Ablation bf Murine Melanomas with Melanocyte-Stimulating Hormone Analog—Conjugated Hollow Gold Nanospheres, Clinical Cancer Research February 2009 15;876

Fujila H, Motokawa T, katagiri T, Yokota S, Yamamoto A, Himeno M. Tanaka Y., Inulavocin. nielanogenesis inhibitor, leads to mistargeting of tyrosinase to lysosomes and accelerates its degradation. J Invest Dermatol. 2009 June; 129(6):1489-99. Epub 2008 Dec. 25

I lac Jung Paik 1. hui Dong Kang 2 3, Jin Seok Choil, Byung Gil Choil and Hye Bin Yim 4, Effect of botulinum a toxin injection on the extraocular muscle fiber layers: Comparison between subtenon injection and intramuscular injection, Japanese Journal of Ophthalmology, Volume 53, Number 3/May, 2009

Thomas R, Mathai A, Braganza A, Billson F. Periodic alternating nystagmus treated with retrobulbar botulinum toxin and large horizontal muscle recession. Indian J Ophthalmol.

Jennifer G. Christie and Uday B. Kompella, Ophthalmic Light Sensitive Nanocarrier Systems, Drug Discov Today. 2008 February; 13(3-4): 124-134.

Martin HrubY, Cestmir Konak and Karel Ulbrich, Polymeric micellar pH-sensitive drug delivery system for doxorubicin, Journal of Controlled Release, Volume 103, Issue 1, 2 March 2005. Pages 137-148.

K. S. Soppiniath, D. C.-W. Tan, Y.-Y. Yang, pH-Triggered Thermally Responsive Polymer Core-Shell Nanoparticles for Drug Delivery, Volume 17 Issue 3, Pages 318-323.

Maha Saad, Olga B. Garbuzenko, Elizabeth Ber, Pooja Chandha, Jayant J. Khandare, Vitaly P. Pozharov, Tamara Minko, Receptor targeted-polymers, dendrimers, liposomes: Which nanocarrier is the most efficient for tumor-specific treatment and imaging? Journal of Controlled Release, Vol. 130, No. 2. (10 Sep. 2008), pp. 107-114

Patri A K, Kukowska-Latallo J F, Baker J R Jr., Targeted drug delivery with dendrimers: comparison of the release kinetics of covalently conjugated drug and non-covalent drug inclusion complex, Adv Drug Deliv Rev. 2005 Dec. 14;57(15):2203-14.

Kerstin Bergh, Parri Wentzel,Johan Stjernschantz. Journal of Ocular Pharmacology and Therapeutics. October 2002, 18(5): 391-400.

Kerstin Bergh, Parri Wentzel, Johan Stjernschantz. Journal of Ocular Pharmacology and Therapeutics. October 2002, 18(5): 391-400

Saad et al., Receptor Targeted Polymers, Denderimers, Lipsomes: Which Nanocarrier Is the Most Efficient for Tumor-Specific Treatment and Imaging? J. of Controlled Release, Vol. 130, No. 2. (10 Sep. 2008), pp. 107-114

Patri A K, Kukowska-Latallo J F, Baker J R Jr., Targeted drug delivery with dendrimers: comparison of the release kinetics of covalently conjugated drug and non-covalent drug inclusion complex., Adv Drug Deliv Rev. 2005 Dec. 14;57(15):2203-14. Epub 2005 Nov. 14.

O Kotrotsiou, K Kotti, E Dini, O Kammona and C Kiparissides, Nanostructured materials for selective recognition and targeted drug delivery, Journal of Physics: Conference Series 10 (2005)281-284

Jan Borovansky, Zinc in pigmented cells and structures, interactions and possible roles. Sborn. lek. Vol. 95 (1994) No. 4. p. 300-320

Angel L. Rosas, 'Joshua D. Nosanchuk, and Arturo Casadevall, Passive Immunization with Melanin-Bindining monoclonal Antibodies Prolongs Survival of Mice with Lethal *Cryptococcus neoformans* Infection, Infect Immun. 2001 May; 69(5): 3410-3412.

Revskaya L, Jongco A M, Sellers R S, howell R C, Koba W, (iuimaraes A J, Nosanchuk J D, Casadevall A, ftidachova L. Radioimmunotherapy 1)1\pdll neat al human metastatic melanoma with melanin-binding antibodies and in combination with dacarbazine. Clin Cancer Res. 2009 Apr. 1;15(7):2373-9. Epub 2009 Mar. 17.

LEN W. SEYMOUR/PAULINE A. FLANAGAN, AYMEN AL-SHAMKIIANI, VLADIMIR SUBR, KAREL ULBRILI I. JAM IS (ASSII)Y, RUTH DUNCAN. Selective Cancer Therapeutics. Summer 1991, 7(2): 59-73.

Pavel Bro2a , Samantha M. 13enitob, CheeLoong Sawa, c, Peter Burgera, c, Harald Heiderd, Matthias Pfisterere, Stephan Marscha, Wolfgang Meierb, c, and Patrick Hunziker, Cell targeting by a generic receptor-targeted polymer nanocontainer platform, Journal of Controlled Release, Volume 102, Issue 2; 2 Feb. 2003, Pages 475-488

Vladimir Torchilin, Antibody-modified liposomes for cancer chemotherapy, Expert Opinion on Drug Delivery, September 2008, Vol. 5, No. 9 : Pages 1003-1025

Singh Shakti K, Lohiya G K, Limburkar P P, Dharbale N B, Mourya V K, Dendrimer a versatile polymer in drug delivery, 2009, Volume 3, Issue Number 3, Page 178-187

Konstas A G, Marshall G E, Lee W R., Immunocytochemical localisation of collagens (I-V) in the human iris, Graefes Arch Clin Exp Ophthalmol. 1990; 228(2): 180-6.

Herbert E. Kaufman MD, Michael S. Insler MD, Hosan A. Ibrahim-Elzembely MD and Stephen C. Kaufman MD, Human fibrin tissue adhesive for sutureless lamellar keratoplasty and scleral patch adhesion: a pilot study, Ophthalmology, Volume 110, Issue 11, November 2003, Pages 2168-2172.

Richard Horobin, John Kiernan, Conn's Biological Stains: A Handbook of Dyes, Stains and Fluorochromes for Use in Biology and Medicine, Taylor and Francis; 1st edition (Jun. 30, 2002)

Aldo Jesorka and Owe Orwar, Liposomes: Technologies and Analytical Applications, Annual Review of Analytical Chemistry Vol. 1: 801-832 (Volume publication date July 2008)

William A. Hare, Elizabeth WoldeMussie. Ronald K. Lai, Hau Ton, Guadalupe Ruiz, Teresa Chun and Larry Wheeler. Efficacy and Safety of Memantine Treatment for Reduction of Changes Associated with Experimental Glaucoma in Monkey, I: Functional Measures, Investigative Ophthalmology-and Visual Science. 2004; 45: 2625-2639.1

62. Jim Hee Kim, Seung Hwa Back. Dong Hyun Kim, Tac Young Choi, Tae Jin Yoon, Jae Sung Hwang. Mee Ree Kim, Ito Jeong Kwon and Choong Hwan Lee. Downregulation of Melanin Synthesis by I laginin A and Its Application to In Vivo Lightening Model, Journal of Investigative Dermatology: (2008) 128, 1227-1235

Rohnov-Jessen I. et al. A fibroblast-associated antigen. charaterization in fibroblasts and immunoreactivity in smooth muscle differentiated stromal cells. J Histochem Cytochem 40: 475-86 (1992).

Singer K H et al. Removal of fibroblasts from human epithelial cell cultures with use of a complement fixing monoclonal antibody reactive with human fibroblasts and monocytes/macrophages. J Invest Dermatol 92: 166-70 (1989).

Toshihiko Hoashi, Kunihiko Tamaki, and Vincent J. Hearing, The secreted form of a melanocyte membrane-bound glycoprotein (Pmel 17/h 100), is released by ectodomain shedding, Published online before print Nov. 2, 2009 as doi 10.1096/6.09-140921

Yeon Mi Kim, Jieun Yun, Chong-Kil Lee, Hwanghee Lee, Kyung Rak Min and Youngsoo Kim, Oxyresveratrol and Hydroxystilbene Compounds Inhibitory Effect on Tyrosinase and Mechanism of Action, The Journal of Biological Chemistry, May 3, 2002, 277, 16340-16344

Raper, H. S. The anaerobic oxidases. Physiol. Rev. 1928, 8, 245-282.

Mason, H. S. The chemistry of melanin. III. Mechanism of the oxidation of trihydroxyphenylalanine by tyrosinase. J. Biol. Chem. 1948, 172, 83-99.

Cooksey, C. J.; Garratt, P. J.; Land, E. J.; Pavel, S.; Ramsden, C. A.; Riley, P. A.; Smit N. P. M. Evidence of the indirect formation of the catecholic intermediate substrate responsible for the autoactivation kinetics of tyrosinase. J. Biol. Chem. 1997, 272, 26226-26235.

Schallreuter, K. U.; Kothari, S.; Chavan, B.; Spencer, J. D. Regulation of melanogenesis-controversies and new concepts. Exp. Dermatol. 2008, 17, 395-404.

71 Halaban, R.; Patton, R. S.; Cheng E.; Svedine, S.; Trombetta, E. S.; Wahl; M. L.; Ariyan, S.; Hebert, D. N. Abnormal acidification of melanoma cells induces tyrosinase retention in the early secretory pathway. J. Biol. Chein. 2002; 277; 148-21-14828.

Aries, F.; Castafier, M.; Gil, M. I. Review: enzymatic browning in minimally processed fruit and vegetables. J. Agric. Food Chem. 1998, 4, 377-389.

Rescigno. A.; Sollai F.; Pisu, B.; A; Sanjust, E. Tyrosinase inhibition: general and applied aspects. J. Enzyme Inhih. Med. Chem. 2002./7, 207-218.

Kim, Y. J.: Uyania. Tyrosinase inhibitors from natural and synthetic sources: structure, inhibition mechanism and perspective for the future. Cell Mol. life sci (2005, 62, 1707-1723.

Parvez, S. Kang, M.; Chung, H. S.; Bae, H. Naturally occurring tyrosinase inhibitors: mechanism and applications in skin health, cosmetics and agriculture industries. Phytother. Res. 2007, 21, 805-816.

Briganti, S.; Camera, E.; Picardo, M. Chemical and instrumental approaches to treat hyperpigmentation. Pigment Cell Res. 2003, 16, 101-110.

Rendon, M I, Gaviria, J. I. Review of skin-lightening agents. Dermutol. Sing. 2005; 31, 886-889. Int. J. Mol. Sci. 2009, 10 2466

Draelos, Z. D. Skin lightening preparations and the hydroquinone controversy. Dermatol. Ther. 2007, 20,308-313.

Parvez, S.; Kang, M.; Chung, H. S.; Cho, C; Hong, M. C.; Shin, M. K.; Roc, U. Survey and mechanism of skin depigmenting and lightening agents. Phytother. Res. 2006, 20, 921-934.

Solano, F.; Briganti, S.; Picardo, M.; Ghanem, G. Hypopigmenting agents: an updated review on biological, chemical and clinical aspects. Pigment Cell Res. 2006, 19, 550-571.

Ando, H.; Kondoh, H.; Ichihashi, M.; Hearing, V. J. Approaches to identify inhibitors of melanin biosynthesis via the quality control of tyrosinase. Invest. Dermatol. 2007, 127, 751-761.

Zhu, W.; Gao, J. The use of botanical extracts as topical skin-lightening agents for the improvement of skin pigmentation disorders. J Investig. Dermutol. Symp. Proc. 2008,/3, 20-24.

Sanchez-Ferrer, A.; Rodriguez-Lopez, J. N., Garcia-Canovas, F.; Garcia-Carmona, F. Tyrosinase: a comprehensive review of its mechanism. Biochim. Biophys. Acta. 1995, 1247, 1-11.

Seo, S. Y.; Sharma, V. K.; Sharma, N. Mushroom tyrosinase: recent prospects. J. Agile. Food Chem. 2003, 51, 2837-2853.

Sugumaran, M. Comparative biochemistry of eumelanogenesis and the protective roles of phenoloxidase and melanin in insects. Pigment Cell. Res. 2002, 15, 2-9.

Matoba, Y.; Kumagai, T.; Yamamoto, A.; Yoshitsu, H.; Sugiyama, M. Crystallographic evidence that the dinuclear copper center of tyrosinase is flexible during catalysis. J. Biol. Chem. 2006, 281, 8981-8990.

Wang, N.; Hebert, D. N. Tyrosinase maturation through the mammalian secretory pathway: bringing color to life. Pigment Cell Res. 2006, 19, 3-18.

Garcia-Molina. F.; Munoz. J. L; Varon. Rodriguez-Lopez, J. N.; Garcia-Canovas. F.; Tudela. J. A review on spectrophotometric measuring the monophenolase and dipheliolase activities of tyrosinase. J. Agric. Food Chem. 2007, 55, 9739-9749.

Garciai-Borron, J. C.; Solano. F. Molecular anatomy of tyrosinase and its related proteins: Beyond the histidine bound metal catalytic center. Pigm. Cell Res. 2002, 15, 162-173.

Wilcox, D. E.; Porras, A. G; Hwang, Y. 1.; Lerch, K.; Winkler, M. E.; Solomon, E. I. Substrate analogue binding to the coupled binuclear copper active site in tyrosinase. J. Am. Chem. 1985, 107, 4015-4027.

Chen, J. S.; Wei, C; Marshall, M. R. Inhibition mechanism of kojic acid on polyphenol oxidase. J. .1.grie. Food Chem. 1991, 39,1897-1901.

Cabanes, J.; Chazarra, S.; Garcia-Carmona, F. Kojic acid, a cosmetic skin whitening agent, is a slow-binding inhibitor of catecholase activity of tyrosinase. J. Phurm. Pharmucol. 1994,46, 982-985.

Espin, J. C.; Wichers, H. J. Slow-binding inhibition of mushroom (Agurieus bispor tyrosinase isoforms by tropotone. J. Agric. Food Chem. 1999, 47, 2638-2644.

Cabanes, J.; Garcia-Canovas, F.; Tudela, J.; Lozano, J. A.; Garcia-Cannona, F. L-mimosine a slow-binding nhibitor of mushroom tyrosinase. Phylochemistry 1987, 26, 917-919.

Harhorne, J. B.; Williams; C. A. Advances in flavonoid research since 1992. Phytochemistry 2000; 55,481-504.

Kubo, I.; Kinst-Hori, Flavonols from saffron flower: tyrosinase inhibitory activity and inhibition mechanism. J. Agric. Food Chem. 1999, 47, 4121-4125.

Kubo, I.; Kinst-Hori, I.; Chaudhuri; S. K.; Kubo, Y.; Sanchez, Y.; Ogura, T. Flavonols from Heterotheca inuloides: tyrosinase inhibitory activity and structural criteria. Bioorg. Med. Chem. 2000, 8, 1749-1755.

Xie, L. P.; Chen, Q. X.; Huang, H.; Wang, H. Z.; Zhang, R. Q. Inhibitory effects of some flavonoids on the activity of mushroom tyrosinase. Biochemistry 2003, 68, 487-491.

Matsuda, H.; Higashino, M.; Chen, W.; Tosa, H.; Iinuma, M.; Kubo, M. Studies of cuticle drugs from natural sources. III. Inhibitory effect of *Myrica rubra* on melanin biosynthesis. Biol. Phurm. Bull. 1995, 18, 1148-1150.

Nugroho, A.; Choi, J. K.; Park, J. H.; Lee, K. T.; Cha, B. C.; Park, H. J. Two new flavonol glycosides from *Lamium amplexicaule* L. and their in vitro free radical scavenging and tyrosinase inhibitory activities. Planta Med. 2009, 75, 364-366.

Gao, H.; Nishida, J.; Saito, S.; Kawabata, J. Inhibitory effects of 5,6,7-trihydroxyflavones on tyrosinase. Molecules 2007, 12, 86-97.

Zhang. C.; Lu. Y. Tan X. Thyrosinase Inhibitory effects and inhibition mechanisms of nobiletin and hesperidin from Citrus peel crude extract. Pharm. Bull. 2009, 32, 410-415.

Itoh, K.; Hirata, N et al; Inhibitory effect of Citrus hassaku extract. Biol. Pharm. Bull. 2009,32,410-415

Lee. S. H.; Choi, S. Y.; Kim, H.; Hwang, J. S.; Lee. B. Ci.; Gao, J. J.; Kim, S. Y. Mulberroside F isolated from the leaves of *morus alba* inhibits melanin biosynthesis. Biol. Phartn. Bull. 2002, 25, 1045-1048

Ryu, Y. B.; Ha, T. J.; Curtis-Long, M. J.; Ryu, H. W.; Gal, S. W.; Park, K. H. Inhibitory effects on mushroom tyrosinase by flavones from the stein barks of Monts Thou (S.) Koidz. J. Enzyme Inhih. Med. Chem. 2008, 23, 922-930.

Shin, N. H.; Ryu; S. Y.; Choi, E. J.; Kang, S. H.; Chang, I. M.; Min, K. R.; Kim, Y. Oxyresveratrol as the potent inhibitor on dopa oxidase activity of mushroom tyrosinase. Biochem. Biophys. Res. Comm//n. 1998; 243, 801-803.

Jeong, S. H.; Ryu, Y. B.; Curtis-Long, M. J.; Ryu, H. W.; Baek, Y. S.; Kung, J. E.; Lee, W. S.; Park, K. H. Tyrosinase Inhibitory Polyphenols from Roots of Monts Ihou J. Agile. Food Chem. 2009, 57, 1195-1203.

Arung, E. T.; Shimizu, K.; Kondo, R. Inhibitory effect of artocarpanone from Art/cu/pus *heterophyllus* on melanin biosynthesis. Biol. Pharm. Bull. 2006, 29, 1966-1969.

Zheng, Z. P.; Cheng, K. W.; To, .1.T.; Li, H.; Wang, M. Isolation of tyrosinase inhibitors from *Artocarpus heterophyllus* and use of its extract as antibrowning agent. Mol. Nutr. Food Res. 2008, 52, 1530-1538.

Karioti, A.; Protopappa, A.; Megoulas, N.; Skaltsa, H. Identification of tyrosinase inhibitors from *Marrubium velutinum* and *Marrubium cylleneum*, Bioorg. Med. Chem. 2007, /5, 2708-2714.

Kim, D.; Park, J.; Kim, J.; Han, C; Yooh, J.; Kim, N.; Seo, J.; Lee, C. Flavonoids as mushroom tyrosinase inhibitors: A fluorescence quenching study. J. Agric. Food Chem. 2006, 54, 935-941.

Miyazawa, M.; Tamura, N. inhibitory compound of tyrosinase activity from the sprout of *Polygonum hydropiper* L. (Benitade). Biol. Pharm. Bull. 2007, 30, 595-597. Int. J. Mol. Si 2009, 10 2468

An, S. M.; Kim, H. J.; Kim, L E.; Boo, ,/.C. Flavonoids, taxifolin and luteolin attenuate cellular melanogenesis despite increasing tyrosinase protein levels. Phytother. Res. 2008, 22, 1200-1207.

Masuda, T.; Yamashita. Screening for tyrosinase inhibitors among extracts of seashore plants and identification of potent inhibitors. Biosci. Biochem. 2005 69,197-201.

Yokota, T.; Nishio, 11. Kubota. . The inhibitory effect of glabridin from licorice extracts Pigment Cell Research, 1998, II, 355-361.

Nerya, O.; Vaya, J.; Musa, K.; Ben-Ark, R.; Tarnir, S. Grahrene and isoliquiritigenin as tyrosinase inhibitors from Licorice roots. J. Agric. Food Chem. 2003, 51, 1201-1207.

Kim, H. J.; Seo, S. H.; Lee, B. G.; Ice, Y. S. Identification of tyrosinase inhibitors from *Glycyrrhiza uralensis*. Planta Med. 2005, 71, 785-787.

Chang, T. S.; Ding, H. Y.; Lin, H. C. Identifying 6,7,4'-trihydroxyisollavone as a potent tyrosinase inhibitor. Biosci. Biotechnol., Biochem. 2005, 69, 1999-2001.

Chang, T. S.; Ding, H. Y. ; Tai, S. S. K.; Wu, C. V. Tyrosinase inhibitors isolated from soygerm koji fermented with *Aspergillus oryzae* BCRC 32288 Food Chem. 2007, 105, 1430-1438.

Chang, T. S. Two potent suicide substrates of mushroom tyrosinase: 7,8,4'-trihydroxyisoflavone and 5,7,8,4'-tetrahydroxyisollavone. J. Agile. Food Chem. 2007, 55, 2010-2015.

Kim, J. H.; Back, S. H.; Kim, D. H.; Choi, T N.; Yoon, T. J.; Hwang, J. S.; Kim, M. R.; Kwon, H. J.; Lee, C. H. Downregulation of melanin synthesis by haginin A and its application to in vivo lightening model. J. Invest. Dermatol. 2008, 128, 1227-1235.

Back, S.; Kim, J.; Kim, D.; Lee, C.; Kim, J.; Chung, D. K.; Lee, C. Inhibitory effect of dalbergioidin isolated from the trunk of *Lespedeza cvrtohotrya* on melanin biosynthesis. J. Microhiol. Biotechnol. 2008, 18, 874-879.

Kim, J. H.; Kim, M. R.; Lee, E. S.; Lee, C. H. Inhibitory effects of calycosin isolated from the root of *Astragalus membrunaceus* on melanin biosynthesis. Biol. Pharm. Bull. 2009, 32, 264-268.

Fu, B.; Li, H.; Wang, X.; Lee, F. S.; Cui, S. Isolation and identification of flavonoids in licorice and a study of their inhibitory effects on tyrosinase. J. Agric. Food Chem. 2005, 53, 7408-7414.

Kim, S. J.; Son, K. H.; Chang, H. W-; Kang, S. S.; Kim, H. P. Tyrosinase inhibitory prenylated flavonoids from *Sophora flavescens*. Biol. Pharm. Bull. 2003, 26, 1348-1350.

Hyun, S. K.; Lee, W. H.; Jeong, da. M.; Kim, Y.; Choi, J. S. Inhibitory effect of kurarinol, kurarindinol, and trifolirhizin from *Sophora flavescens* on tyrosinase and melanin synthesis. Biol. Pharm. Bull. 2008, 31,154-158.

Zhang. X et al. Inhibitory effect of 2,4,2,4 tetrahydroxy-3-(3-methyl-2-butenyl) chalcone on tyrosinase activity and melanin biosynthesis. Biol. pharm. Bull. 2009, 32, 86-90.

Shimizu, K.; Konklo. R.; Sikai. K. Inhibition of tyrosinase by flavonoids, stilbenes and related 4-substituted resorcinols: structure-activity investigations. Planta Med. 2000, 66, 11-15.

Chen, Q. X.; Ke, L. N.; Song, K. K.; Ituang, H.; Liu, X. D. Inhibitory effects of hexylresorcinol and dodecyiresorcinol on mushroom (*Agaricus bisporus*) tyrosinase. Protein J. 2004, 23, 135-141.

Nerya, O.; Musa, R.; Khatib, S.; Tamir, S.; Vaya, J. Chalcones as potent tyrosinase inhibitors: the effect of hydroxyl positions and numbers. Phytochcinistty 2004, 65, 1389-1395.

Khatih, S.; Nerya, O.; Musa, R.; Shmuel, M.; Tamir, S.; Vaya, J. Chalcones as potent tyrosinase inhibitors: the importance of a 2,4-substituted resorcinol moiety. Bioorg. Med. Chem. 2005, 13, 433-441.

Jun, N.; Hong, G.; Jun, K. Synthesis and evalution of 21,4',61-trihydroxychalcones as a new class of tyrosine inhibitors. Bioorg. Med. Chem. 2007, 15, 2396-2402.

Cho, Si., Rob, J. S.: Sun, W. S.; Kim, S. H.; Park, K. D. N-Benzylbenzamides: a new class of potent tyrosinase inhibitors. Bioorg. Med. Chem. Lett. 2006, 16, 2682-2684.

Khatib, S.; Nerya, O.; Musa, R.; Tamir, S.; Peter, T.; Vaya, J. Enhanced substituted resorcinol hydrophobicity augments tyrosinase inhibition potency: J. Med. Chem. 2007, 50,2676-2681.

Kim, Y. M.; Yun, J.; Lee, C. K.; Lee, H.; Min, K. R.; Kim, Y. Oxyresveratrol and hydroxystilbene compounds. Inhibitory effect on tyrosinase and mechanism of action. J. Biol. Chem. 2002, 277, 16340-16344.

Kuniyoshi, S.; Seiji, Y.; Ryuichiro, K. A new stilbene with tyrosinase inhibitory activity form *Chlorophoru excelsa*. Chem. Phurin. Bull. 2003, 51, 318-319.

Ohguchi, K.; Tanaka, T.; Iliya, 1.; Ito, T.; linuma, M.; Matsumoto, K.; Akao, Y.; Nozawa, Y. Gnetol as a potent tyrosinase inhibitor from genus *Gnetum*. Biosci. Biotechnol., Bioehem. 2003, 67, 663-665.

Yokozawa, T.; Kim, Y. J. Piceatannol inhibits melanogenesis by its antioxidative actions. Biol. Phurm. Bull. 2007, 30, 2007-2011.

Ohguchi, K.; Tanaka, T.; Kido, T.; Baba, K.; Iinuma, M., Matsumoto, K.; Akao, Y.; Nozawa, Y. Effects of hydroxystilbene derivatives on tyrosinase activity. Biochem. Biophys. Res. Commun. 2003, 307, 861-863.

Song. K. K. et al; Inhibitory effect of cis- and trans-isomers of 3.5-dihydroxystibene on the activity of mushrum tyrosinase, Biochem. Biophys. Res. Commun. 2006, 342, 1147-1151, Likhitwitayavuid, K.; Sornsute, A.; Sritularak. li.; Ploypradith, P. Chemical transformations of oxyresveratrol (trans-2,4,3'5'-tetrahydroxystilbene), into a potent tyrosinase inhibitor and a strong cytotoxic agent. Bioorg. Med. Chem. Lett. 2006, 16, 5650-5653.

142. Oozeki, H.; Tajima, R.; Nihei, K. Molecular design of potent tyrosinase inhibitors having the bibenzyl skeleton. Bioorg. Med. Chem. Lett. 2008,18, 5252-5254.

Vielhaber, G.; Schmaus, G.: Jacobs, K.; Franke, I I.; Lange, S.; Herrmann, M.; Joppe, H.; Koch, 0. 4-(1-Phenylethy1)1,3-benzenediol; a new, highly efficient lightening agent. Int. J. Cosine!.Sci. 2007, 29, 65-66.

Song, S.; Lee, H.; Jin, Y.; Ha, Y. M.; 13ae. S.; Chung, H. Y.; Suh, H. Syntheses of hydroxy, substituted 2-phenyl-naphthalenes as inhibitors of tyrosinase. Bioorg. Med. Chem. Lett. 2007, 17, 461-464.

Ha, Y. M.; Chun S. W.; Song, S.; Lee, H.; Suh, H.; Chung H. Y. 4-(6-Hydroxy-2-naphthyl)-1,3-bezendiol a potent, new tyrosinase inhibitor. Thai. Phurtn. Bull. 2007, 30, 1711-1715.

Jones, K.; Hughes, J.; Hong, M.; Jia, Q.; Orndorff, S. Modulation of melanogenesis by aloesin: a competitive inhibitor of tyrosinase. Pigment Cell Res. 2002, 15, 335-340.

Choi, S.; Lee, S. K.; Kim, J. E.; Chung, M. N.; Park, Y. 1. Aloesin inhibits hyperpigmentation induced by UV radiation. Clin. Exp. Dermutol. 2002, 27, 513-515.

Masamoto, Y.; Ando, H.; Murata, Y.; Shimoishi, Y.; Tada, M.; Takahata, K. Mushroom tyrosinase inhibitory activity of esculetin isolated from seeds of *Efrphorbia luthyris* L. Biosci. Biotechnol., Biochem. 2003, 67, 631-634.

Sollai, F.; Zucca, P.; Sanjust, E.; Steri, D.; Resciqno, A. Umbelliferone and esculetin: inhibitors or substrates for polyphenol oxidases? Biol: Phurm. Bull. 2008, 31, 2187-2193.

Piao, X. L.; Baek, S. H.; Park, M. K.; Park, J. H. Tyrosinase-inhibitory furanocoumarin from *Angelica duhuricu*. Biol. Phurni. Bull. 2004, 27, 1144-1146.

Ahmad, V. U.; Ullah, F.; Hussain, .1.; Farooq, U.; Zubair, M.; Khan, M. T.; Choudhary, M. I. Tyrosinase inhibitors from *Rhododendron collettianum* and their structure-activity relationship (SAR) studies. Chem. Pharm. Bull. 2004, 52, 1458-1461.

Lee, H. S. Tyrosinase inhibitors of *Pulsatilla cernua* root-derived materials. J. Agric. Food Chem. 2002, 50, 1400-1403.

Jimenez, M.; Chazarra, S.; Escribano, J.; Cabanes, J.; Garcia-Carmona, F. Competitive inhibition of mushroom tyrosinase by 4-substituted benzaldehydes. J. Agric. Food. Chem, 2001, 49, 4060-4063.

Kubo. 1.; Kinst-Hori et al; a potent tyrosinase inhibitor from African medicinal plants. Planta Med. 1999, 65, 19-22.

Lim, J. Y.; Ishiguro, K.; Kubo, 1. Tyrosinase inhibitory p-coumaric acid from ginseng leaves. Phytoter. Res. 1999,13, 371-3

Iwai, K.; Kishimoto, N.; Kakino. Y.; Mochida, K.; Fujita, T. hi vitro antioxidative effects and tyrosinase inhibitory activities of seven hydroxycinnamoyl derivatives in green coffee beans. j. Agric food Chem. 2004, 52, 4891-4898.

Miyazawaa. M.; Oshima; T.; Koshino. K.; Itsuzaki, Y.; Anzai, J. Tyrosinase inhibitor from black rice bran. J. Agric. Food. Chem. 2003, 51, 6953-6956.

Kubo, I.; Kinst-Hori, I. Tyrosinase inhibitors from cumin. Agric. Food Chem. 1998, 46, 5338-5341.

Kubo, I.; Kinst-Hori, I. Tyrosinase inhibitory activity of the olive oil flavor compounds. .1. Agric. Food Chem. 1999, 47, 4574-4578.

Conrad, Dawso, S. R.; Hubbard, E. R.; Meyers; T. E.; Strothkamp, K. G. Inhibitor binding to the binuclear active site of tyrosinase: temperature, pH and solvent deuterium isotope effects. Biochemistry 1994; 33, 5739-5744.

Huang, X. H., Chen, Q. X., You, M. S.; Wang, Q.; Song, K. K., Wang, J.; Sha, L; Guan, X. Inhibitory effects of flubrobenzaldehydes on the activity of mushroom tyrosinase. J. Enzyme Minh. Med. Chem. 2006, 21, 413-418.

Huang, Q. S.; Z-Y. J.; Li, H I.; Zhuang, J. X.; Zhang, C. L.; Zhou, .I. J.; Li, W. G.; Chen, Q. X. Inhibitory effects of methyl trans-cinnamate on mushroom tyrosinase and its antimicrobial activities. J. Agric. Food Chem. 2009, 57, 2565-2569.

Zhang, J. P.; Chen, Q. X.; Song, K. K.; Xie, J. J. Inhibitory effects of salicylic acid family compounds on the diphenolase activity of mushroom tyrosinase. Food Chem. 2006, 95, 579-584.

Kanade, S. R.; Suhas, V. L., Chandra, N.; Gowda, L. R. Functional interaction of diphenols with polyphenol oxidase. Molecular determinants of substrate/inhibitor specificity. FEBS J. 2007, 274, 4177-4187.

Masuda, T.; Fujita, N.; Odaka, Y.; Takeda, Y.; Yonemori, S.; Nakamoto, K.; Kuninaga, H. Tyrosinase inhibitory activity of ethanol extracts from medicinal and edible plants cultivated in okinawa and identification of a water-soluble inhibitor from the leaves of Nundina domestica. Biosci. Biotechnol., Biochem: 2007, 7/, 2316-2320.

Kang, H. S.; Choi, J. H.; Cho, W. K.; Park, J. C.; Choi, J. S. A sphingolipid and tyrosinase inhibitors from the fruiting body of Phellinus linteus. Arch. Pharm. Res. 2004, 27, 742-750.

No, J. K.; Kim, M. S.; Kim, Y. J.; Bae, S. J.; Choi, J. S.; Chung; H. Y. Inhibition of tyrosinase by protocatechuic aldehyde. Am. J. Chin. Med. 2004, 32; 97-103;

Song, K. K.: Chen, Q. X.; Wang, Q.; Qiu, L.; Inhibitory effects of 4-vinylbenzaldehyde and 4-vinylbenzoic acid on the activity of mushroom tyrosinase. J. Enzyme Inhib. Med. Chem. 2005, 20, 239-243.

Xue. C. B.: Luo, W. C:; Ding. Q.; Liu, S. Z.; Ciao: X. X. Quantitative structure-activity relationship studies of mushroom tyrosinase inhibitors J. Comput. Aided. Mol. Des. 2008, 22, 299-309.

Chen, Q. X.; Song, K. K.; Wang, Q.; Huang, H. Inhibitory effects on mushroom tyrosinase by some alkylbenzaldehyde. J. Enzyme. Inhib. Med. Chem. 2003, 18.491-496.

Nihei, K.; Vamagiwa, Y.; Kamikawa, T.; Kubo, 1,2-Hydroxyl-4-isopropylbenzaldehyde, a potent partial tyrosinase inhibitor. Bioorg. Med. Chem. Lett. 2004, 14, 681-683.172:

Lev, .I. P.; Bertram, 11.1. Hydroxy- or methoxy-substituted benzaldoximes and benzaldehyde-O-alkyloximes as tyrosinase inhibitors. Bioorg. Med. Chem. 2001, 9, 1879-1885.

Xue, C. B.; Zhang, L.; Luo, W. C.; Xie, X. Y., Jiang, L.; Xiao, T. 3D-QSAR and molecular docking studites of benzaldehyde thiosemicarbazone, benzaldehyde, benzoic acid, and their derivatives as phenoloxidase inhibitors. Bioorg. Med. Chem. 2007, /5, 2006-2015.

Kubo, 1.; Kinst-Hori, I.; Kubo ,Y., Yamagiwa, Y.; Kamikawa, T.; Haraguchi, H. Molecular design of anti-browning agents. ,I Agric. Food Chem. 2000, 48, 1393-1399.

Kubo, 1.; Kinst-Hori, 1.; Nihei, K.; Soria, F.; Takasaki, M.; CalderOn, J. S.; Cespedes, C. L. Tyrosinase inhibitors from galls of Rhus javanica leaves and their effects in insects.

Z. Naturforsch., C 2003, 58, 719-725.

Kubo, I.; Chen, Q. X.; Nihei, K. Molecular design of antibrowning agents: antioxidative tyrosinase inhibitors. Food Chem. 2003, 81, 241-247.

Kang, N. H.; Rho, H. S.; Hwang, J. S.; Oh, S. G. Depigmenting activity and low cytotoxicity of alkoxy benzoates or alkoxy cinnamte in cultured melanocytes. Chem. Phurtn.; Bull. 2003, 51, 1085-1088.

Nithitanakool, S.; Pithayanukul, P.; Bavovada, R.; Saparpakorn, P. Molecular docking studies and anti-tyrosinase activity of Thai mango seed kernel extract. Molecules 2009, 14, 257-265.

No, J. K.; Soung, D. Y.; Kim,. /I; Shim, K. H.; Jun, Y. S.; Rhee, S. H.; Yokozawa, T.; Chung, H. Y. Inhibition of tyrosinase by green tea components. Life Sci.- 1999, 65; 241-246.

Lee, C. W.; Son, E. M.; Kim, H. S.; Xi, p.; Batmunkh, T.; Lee, B. J. Koo, K. A. Synthetic tyrosyl gallate derivatives as potent melanin formation inhibitors. Bioorg. Med. Chem. Lett. 2007, /7, 5462-5464.

Ding, H. Y.; Lin, H. C.; Chang, T. S. Tyrosinase inhibitors isolated from the roots of Paeonia suffruticosa. Cosmet. Sci. In press.

Jeon. H. J.; Noda. M :Maruyama. M.; Matoha. Y.; Kumagai. T.; Suqivama. M. Identification and kinetic study of tyrosinase inhibitors found in sake lees. J. Agric. Food Chem. 2006, 54, 9827-9833.

Maqid. A. A.; Voutquenne-Nazabadioko, L.; Bontemps. G., Litaudon, M.; Lavaud, C. Tyrosinase inhibitors and sesquiterpene diglycosides from Guioa villosa. Planta Med. 2008, 74, 55-60.

Masuda, T.; Odaka, Y.; Oqawa, N.; Nakamoto, K.; Kuninaqa, H. Identification of geranic acid, a tyrosinase inhibitor in lemongrass (Cymbopogon Citratus). J. Agric. Food Chem. 2008, 56, 597-601.

Sabudak, T.; Khan, M. T.; Choudhary, M A.; Oksuz, S. Potent tyrosinase inhibitors from Trifolium balansae. Nat. Prod. Res. 2006, 20, 665-670.

Khan, S. B.; Azhar-U1-Haq; Afza, N.; Malik, A.; Khan, M. T.; Shah, M R.; Choudhany, M. I. Tyrosinase-inhibitory long-chain esters from Amberboa ramosa. Chem. Pharm. Bull. 2005, 53, 86-89.

Khan, M. T.; Khan, S. B.; Ather, A. Tyrosinase inhibitory cycloartane type triterpenoids from the methanol extract of the whole plant of Amberboa ramosa Jafiri and their structure-activity relationship. Bioorg. Med. Chem. 2006, 14, 938-943.

Khan, M. T.; Choudhary, M. I.; Atta-ur-Rahman; Mamedova; R. P.; Aqzamova, M. A.; Sultankhodzhaev, M. N.; Isaev, M. I. Tyrosinase inhibition studies of cycloartane and cucurbitane glycosides and their structure-activity relationships. Bioorg. Med. Chem. 2006, 14, 6085-6088.

Ullah, F.; Hussain, H.; Hussain, J.; Bukhari, I. A.; Khan, M. T.; Choudhary, M. I.; Gilani, A. H.; Ahmad, V. U. Tyrosinase inhibitory pentacyclic triterpenes and analgesic and spasmolytic activities of methanol extracts of *Rhododendron collettianum*. Phytother. Res. 2007, 21, 1076-1081.

Shaheen, F.; Ahmad, M.; Khan, M. T.; Jalil, S.; Ejaz, A.; Sultankhodjaev, M. N.; Arfan, M.; Choudhary, M. T.; Atta-ur-Rahman. Alkaloids of Aconitum laeve and their anti-inflammatory antioxidant and tyrosinase inhibition activities. Phtochemistry 2005, 66, 935-940.

Sultankhodzhaev, M. N.; Khan, M. T.; Moin, M.; Choudhary, M. I.; Atta-ur-Rahman. Tyrosinase inhibition studies of diterpenoid alkaloids and their derivatives: structure-activity relationships. Nat. Prod. Res. 2005, 19, 517-522.

Li, C. Y.; Lee, E. J.; Wu, T. S. Antityrosinase principles and constituents of the petals of *Crocus sativus*. J. Nat. Prod. 2004, 67, 437-440.

Wu, B.; He, S.; Wu, X. D.; Pan, Y. J. New tyrosinase inhibitory-sesquiterpenes from *Chloranthus hentyi*. Chem. Biodivers. 2008, 5, 1298-303.

Wu, B.; Chen, J.; Qu, H.; Cheng. Y. Complex sesquiterpenoids with tyrosinase inhibitory activity from the leaves of *Chloranthus tianmushanensis*, J. Nat. Prod. 2008, 75, 877-880.

Choudhary, M. I.; Sultan, S.; Khan, M. T.; Ata-ur-Rahman. Microbial transformation of 17alpha-ethynyl- and 17alpha-ethylsteroids, and tyrosinase inhibitory activity of transformed products. Steroids 2005, 70, 798-802.

Leu, Y. L.; Hwang, T. L.; Hu, J. W.; Fang, J. Y. Anthraquinones from *Polygonum cuspidutum* as tyrosinase inhibitors for dermal use. Phytother. Res. 2008, 22, 552-556.

Devkota, K. P.; Khan, M. T.; Ranjit, R.; Lannang, A. M.; Samreen; Choudhary, M. I. Tyrosinase inhibitory and antileishmanial constituents from the rhizomes of *Paris polyphyllu*. Nut. Prod. Res. 2007, 21, 321-327.

Azhar-Ul-Haq; Malik, A.; Khan, M. T.; Anwar-Ul-Haq; Khan; S. B.; Ahmad, A.; Choudhary, M. I. Tyrosinase inhibitory lignans from the methanol extract of the roots of *Vitex negundo* Linn. and their structure-activity relationship. Phytomedicine 2006, 13, 255-260.

Kang, U. S.; Kim, U. K.; Byun, D. S.; Son, B. W.; Nam, T. J.; Choi, J. S. Tyrosinase inhibitors isolated from the edible brown alga *Ecklonia stolonifera*. Arch. Pharm. Res. 2004, 27, 1226-1232.

Li, X.; Kim, M. K.; Lee, U.; Kim, S. K.; Kang, J. S.; Choi, H. D.; Son, B. W. Myrothenones A and B, cyclopentenone derivatives with tyrosinase inhibitory activity from the marine-derived fungus *Myrothecium* sp. Chem. Pharm. Bull 2005, 53, 453-455.

Tsuchiya, T.; Yamada, K.; Minoura, K.; Miyamoto, K.; Usami ,Y.; Kobayashi, T.; Hamada-Sato, N.; Imada, C.; Tsujibo, H. Purification and determination of the chemical structure of the tyrosinase inhibitor produced by *Trichoderma viride* strain H2-7 from a marine environment. Biol. Pharm. Bull. 2008, 31.1618-1620.

Gerdemann, C.; Eicken, C.; Krebs, B. The crystal structure of catechol oxidase: new insight into the function of type-3 copper proteins. Ace. Chem. Res. 2002, 35, 183-191.

Criton, M.; Le Mellay-Hamon V. Analogues of N-hydroxy-N'-phenylthrourea and N-hydroxy-N-phenylurea as inhibitors of tyrosinase and melanin formation. Bioorg. Med. Chem. Lett. 2008, 18, 3607-3610.

Le Mellay-Hamon V.; Criton, M. Phenylethylamide and phenylmethylamide derivatives as new tyrosinase inhibitors. Biol. Pharm. Bull. 2009, 32, 301-303.

Kang, S. S.; Kim, H. J.; Jin, C.; Lee; Y. S. Synthesis of tyrosinase inhibitory (4-oxo-4H-pyran-2-yl) acrylic acid ester derivatives. Bioorg. Med; Chem. Lett. 2009, 19, 188-191.

Xre, L. P.; Chen, Q. X. ; Huang, H.; Liu, X. D.; Chen, H. T.; Zhang, R. Q. Inhibitory effects of cupferron on the monophenolase and diphenolase activity of mushroom tyrosinase. Int. J. Biochem. Cell Biol. 2003, 35, 1658-1666.

Shiino, M.; Watanabe, Y.; Umezawa, K. Synthesis of N-substituted N-nitrosohydroxylamines as inhibitors of mushroom tyrosinasc. Bioorg. Med. Chem. 2001, 9, 1233-1240.

Shiino, M.; Watanabe, Y.; Umwzawa. K. Synthesis of tyrosinase inhibitory activity of novel N-hydroxybehzyl-N-nitrosohydroxylamines. Bioorg. Chem. 2003,.) 1, 129-135.

Shiino, M.; Watanabe, Y.; Umezawa, K. pH-dependent inhibition of mushroom tyrosinase by N-substituted N-nitrosohydroxylamines. J. Enzyme Inhib. Med. Chem. 2008, 23, 16-20.

Khan, K. M.; Maharvi, G. M.; Per\ cell, S.; Khan, M. T.; Abdel-Jalil, R. J., Shah, S. T.; Fecker, M.; Choudhary, Atta-ur-Rahman; Voel ter, W. Synthesis of methyl ether analogues of sildenafil (Viagra) possessing tyrosinase inhibitory potential. Chem. Biodivers. 2005, 2, 470-476.

Khan, M. T.; Choudhary, M. I.; Khan, K. M.; Rani, M.; Atta-ur-Rahman, Structure-activity relationships of tyrosinase inhibitory combinatorial library of 2,5-disubstituted-1,3,4-oxadiazole analogues. Bioorg. Med. Chem. 2005, /3388-3395.

Khan, K. M.; Mughal, U. R.; Khan, M. T.; Zia-Ullah; Perveen, S.; Choudhary, M. I. Oxazolones: new tyrosinase inhibitors; synthesis and their structure-activity. relationships. Bioorg. Med. Chem. 2006, /4, 60276031

Khan et al., Tetraketones: a new class of tyrosinase inhibitors. Bioorg. Med. Chem. 2006, 14, 344-351.

Koketsu et al., Inhibitory effects of 1,3-selenazol-4-one derivatives on mushroom tyrosinase. Chem. Pharm. Bull. 2002, 50, 1594-1596.

Ha et al., Inhibition of tyrosinase activity by N,N-unsubstituted selenourea derivatives. Biol. Pharm. Bull. 2005, 28, 838-840.

Ahn et al., Regulation of melanin synthesis by selenium-containing carbohydrates. Chem. Pharm. Bull. 2006, 54, 281-286.

Kim, Y. J.; No, J. K.; Lee, .1.H.; Chung, H. Y. 1,41-Dihydroxybiphehyl as a new potent tyrosinase inhibitor. Biol. Pharm. Bull. 2005, 28, 323-327.

Dai, Y.; Zhou, G. X.; Kurihara, H.; Ye, W. C.; Yao, X. S. Biphenyl glycosides from the fruit of *Pyracantha fortuneana*. J. Nat. Prod. 2006, 69, 1022-1024.

No, J. K.; Kim, Y. J.; Lee, J. S.; Chung, H. Y. Inhibition of melanogenic activity by 4,4'-dihydroxybiphenyl in melanoma cells. Biol. Pharm. Bull. 2006, 29, 14-16.

Lee, K. H.; Koketsu, M.; Choi, S. Y.; Lee, K. J.; Lee, P.; Ishihara, H.; Kim, S. Y. Potent inhibitory effects of N-aryl S-alkylthiocarbamate derivatives on the dopa oxidase activity of mushroom tyrosinase. Chem. Pharm. Bull. 2005, 53, 747-749.

Kuo, P. C.; Damu, A. G.; Cherng, C. Y.; Jeng, J. F.; Teng, C. M.; Lee, E. J.; Wu, T. S. Isolation of a natural antioxidant, dehydrozingerone from *Zingiber officinale* and synthesis of its analogues for recognition of effective and antioxidant and antityrosinase agents. Arch. Pharm. Res. 2005, 28, 518-528

Tsou, C. L. Kinetics of substrate reaction during irreversible modification of enzyme activity. Adv. Enzymol. Relat. Areas. Mol. Biol. 1988, 61, 381-436.

Espin, I C; Wichers, H J, Effect of captopril on mushroom tyrosinase activity in vitro. Bichim. Biophys. Acta. 2001, 1544, 289-300.

Skotland, T.; Ljones, T. Inactivation of dopamine [ ]-monooxygenase by hydrogen peroxide and by Ascorbate. Arch. Biochem. Biophys. 1980, 201, 81-87.

Andrawis, A.; Kahn, V. Inactivation of mushroom tyrosinase by hydrogen peroxide. Phytochemisity 1985, 24, 397-405.

Schwcikardt, T.; Olivares, C.; Solano, F.; Jaenicke, E.; Garcia-Botron, J. C.; Decker, H. A three-dimensional model of mammalian tyrosinase active site accounting for loss of function mutations. Pigment Cell Res. 2007, 20, 394-401.

Chen, Q. X.; Huang, H.; Kubo, 1. Inactivation kinetics of mushroom tyrosinase by cetylpyridinium chloride. J. Protein Chem. 2003, 22, 481-487.

Qiu, L.; Chen, Q. X.; Wang, Q.; Huang, H.; Song, K. K. Irreversibly inhibitory kinetics of 3,5-dihydroxyphenyl decanoate on mushroom (*Agaricus hisporus*) tyrosinase. Bioorg. Med. Chem. 2005, 13, 6206-6211.

Liu, S. H.; Pan, I. H.; Chu, I. M. Inhibitory effect of p-hydroxybenzyl alcohol on tyrosinase activity and melanogenesis. Biol. Phurm. Bull. 2007, 30, 1135-1139.

Li, B.; Huang, Y.; Paskewitz, S. M. Hen egg white lysozyme as an inhibitor of mushroom tyrosinase. FEBS Lett. 2006, 580, 1877-1882.

Haghbeen, K.; Saboury, A. A.; Karbassi, F. Substrate share in the suicide inactivation of mushroom tyrosinase. Biophys. Acta 2004, 1675, 139-146.

Waley, S. G. Kinetics of suicide substrate: practical procedures for determining parameters. Biochem. J. 1985, 227, 843-849.

Garcia-Canovas, F.; Tudela, J.; Varon, R.; Vazquez, A. M. Experimental methods for kinetic study of suicide substrates. J. Enzyme Inhih. 1989, 3, 81-90.

Land, E. J.; Ramsden. C. A.; Riley, P. A. The mechanism of suicide-inactivation of tyrosinase: a substrate structure investigation. Tohoku J. Exp. Med. 2007, 212, 341-348.

Land, E. J.; Ramsden, C. A.; Riley, P. A.; Stratford, M. R. Evidence consistent with the requirement of cresolase activity for suicide inactivation of tyrosinase. Tohoku J. Exp. Med. 2008, 216, 231-238.

Chang, T. S. 8-Hydroxydaidzein is unstable in alkaline solutions. J. Cosmet. Sci. In press. Shibahara 5, Takeda, K, Yasumoto K, Udono T, Watanabe K, Saito H, Takahashi K. Microphthalmia-associated transcription factor (MITF): Multiplicity in structure, function, and regulation. J. Investig. Dermutol. Symp. Proc. 2001; 6:99-104.

Levy C, Khaled M, Fisher D. MITF: Master regulator of melanocyte development and melanoma oncogene. Trends Mol. Med. 2006; 12:406-414.

Kim D, Park S, Park K. Transforming growth factor-beta1 decreases melanin synthesis via delayed extracellular signal-regulated kinase activation. Int. J. Biochem. Cell Biol. 2004; 36:1482-1491

Yang G, Li Y, Nishimura E, Xin H, Zhou A, Guo Y, Dong L, Denning M, Nickoloff B, Cui R. Inhibition of PAX3 by TGF-beta modulates melanocyte viability. W. Cell. 2008; 32:554-563.

Kim D, Park S, Kwon S, Park E, Huh C, Youn S W, Park K. Sphingosylphosphorylcholine-induced ERK activation inhibits melanin synthesis in human melanocytes. Pigment Cell Res. 2006; 19:146-153

Xu W, Gong L, Haddad M, Bischof O, Campisi J, Yeh E, Medrano E. Regulation of microphthalmia-associated transcription factor MITF protein levels by association with the ubiquitin-conjugating enzyme hUBC9. Exp. Cell Res. 2000; 255:135-143

Barbara Bellei, Enrica Flori, Enzo Izzo, Vittoria Maresca, Mauro Picardo, GSK3[betaTGF inhibition promotes melanogenesis in mouse B16 melanoma cells and normal human melanocytes, Cellular Signalling, Volume 20, Issue 10, October 2008, Pages 1750-1761, ISSN 0898-6568, DOI: 10.1016/j.cellsig.2008.06.001.

DAN-NING H U, STEVEN A. McCORMICK, ALEXANDER Y. LIN, JENNIFER Y. LIN, TGF-beta2 inhibits Growth of Uveal Melanocytes at Physiological Concentrations, Experimental Eye Research, Volume 67, Issue 2, August 1998, Pages 143-150, ISSN 0014-4835, DOI: 10.1006/exer.1998.0501.

Villareal M O, Han J, Yamada P, Shigemori H, Isoda H., Hirseins inhibit melanogenesis by regulating the gene expressions of Mitf and melanogenesis enzymes, Exp Dermatol. 2010 May; 19(5):450-7. Epub 2009 Sep. 17.

Jody P. Ebanks, R. Randall Wickett, and Raymond E. Boissy, Mechanisms Regulating Skin Pigmentation: The Rise and Fall of Complexion Coloration, Int J Mol Sci. 2009 September; 10(9): 4066-4087.

What is claimed is:

1. A method of lightening the color of the iris of a human subject, the method comprising administering to the iris of the human subject an amount of a composition comprising a melanogenesis inhibitor capable of misdirecting tyrosinase to lysosomes and effective to lighten the color of the iris of the human subject, wherein the melanogenesis inhibitor comprises inulavosin.

2. A method of lightening the color of the iris of a human subject, the method comprising administering to the iris of the human subject an amount of a composition comprising inulavosin in an amount effective to lighten the color of the iris of the human subject.

3. The method of any one of claim 1, or 2, wherein the composition is administered in conjunction with an injection of saline, siRNA, botulinum toxin, or a combination of botulinum toxin and siRNA.

4. The method of any one of claim 1, or 2, wherein the composition is administered through a nanoparticle drug delivery system containing a targeting agent of iridial melanocytes.

5. The method of claim 4, wherein the targeting agent comprises a composition of iron, zinc, gold, or a combination thereof.

6. The method of claim 5, wherein the targeting agent comprises zinc oxide.

7. The method of any one of claim 1, 3-6, or 2, wherein the composition is in the form of eye drops.

8. The method of any one of claim 1, 3-6, or 2, wherein the composition is administered through an ophthalmic drug delivery system selecting from the group consisting of salves, creams, emulsions and gels.

9. The method of any one of claims 1, 3-6, or 2 wherein the composition is administered in the fornices under the eyelid.

10. The method of any one of claim 1, 3-6, or 2, wherein the composition is administered through an ophthalmic drug delivery system comprising a time-release coated insert.

11. The method of claim 10, wherein the time-release coated insert is coated on at least one side.

12. The method of any one of claim 1, 3-6 or 2, wherein the subject is a healthy human.

13. The method of any one of claim 1, 3-6, or 2, wherein the subject is afflicted with glaucoma.

14. The method of any one of claim 1, 3-6, or 2 wherein the medication is transported into the anterior chamber of the eye by microneedles.

15. The method of any one of claim 1, 3-6, or 2 wherein the medication is transported into the anterior chamber of the eye by over-saturating the molecule carriers with the medication.

16. The method of any one of claim 1, 3-6, or 2 wherein the medication is transported inside the melanocytes via Folate receptors.

* * * * *